United States Patent
Degani et al.

(10) Patent No.: US 8,200,312 B2
(45) Date of Patent: Jun. 12, 2012

(54) APPARATUS FOR MONITORING A SYSTEM PRESSURE IN SPACE WITH TIME AND METHOD FOR ASSESSING DRUG DELIVERY AND RESISTANCE TO THERAPY AND PRODUCT

(75) Inventors: Hadassa Degani, Rehovot (IL); Yaron Hassid, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 468 days.

(21) Appl. No.: 12/440,066

(22) PCT Filed: Sep. 6, 2007

(86) PCT No.: PCT/IL2007/001102
§ 371 (c)(1),
(2), (4) Date: Jun. 25, 2009

(87) PCT Pub. No.: WO2008/029407
PCT Pub. Date: Mar. 13, 2008

(65) Prior Publication Data
US 2009/0264734 A1   Oct. 22, 2009

Related U.S. Application Data

(60) Provisional application No. 60/824,655, filed on Sep. 6, 2006.

(51) Int. Cl.
*A61B 5/05* (2006.01)
(52) U.S. Cl. .................................... 600/420; 600/458
(58) Field of Classification Search ................. None
See application file for complete search history.

(56) References Cited

U.S. PATENT DOCUMENTS

| | | | | |
|---|---|---|---|---|
| 6,056,738 A | * | 5/2000 | Marchitto et al. | 606/2 |
| 6,272,370 B1 | * | 8/2001 | Gillies et al. | 600/411 |
| 6,464,662 B1 | * | 10/2002 | Raghavan et al. | 604/28 |
| 6,889,072 B2 | * | 5/2005 | Prince | 600/420 |
| 2003/0114751 A1 | * | 6/2003 | Pedain et al. | 600/431 |
| 2006/0073101 A1 | * | 4/2006 | Oldfield et al. | 424/9.34 |
| 2006/0235297 A1 | * | 10/2006 | Kawamoto | 600/431 |

OTHER PUBLICATIONS

International Search Report published May 7, 2009 for PCT/IL2007/001102, filed Sep. 6, 2007.
Written Opinion published Apr. 3, 2009 for PCT/IL2007/001102, filed Sep. 6, 2007.
International Preliminary Report on Patentability published Apr. 7, 2009 for PCT/IL2007/001102, filed Sep. 6, 2007.

(Continued)

*Primary Examiner* — Long V. Le
*Assistant Examiner* — Lawrence Laryea
(74) *Attorney, Agent, or Firm* — Martin Fleit; Paul D. Bianco; Fleit Gibbons Gutman Bongini & Bianco PL

(57) ABSTRACT

A method, apparatus and a computer readable medium containing executable instructions for monitoring a system pressure within a mammal, human or animal, via a tracer/contrast agent, in space in time for determining non-invasively actual interstitial fluid pressure and/or concentration of the tracer/contrast agent. Further, an imaging method, an apparatus and a product for non-invasive mapping of actual interstitial fluid pressure and/or a tracer/contrast agent concentration for assessing drug delivery and resistance to therapy of a tumor or organ within a mammal, to suppress or reduce pressure in a tumor or organ and to control the delivery of drugs to a tumor or organ.

15 Claims, 17 Drawing Sheets

OTHER PUBLICATIONS

European Search Report dated Mar. 26, 2010 for EP07805562.1 (claiming priority to PCT/L07/01102).

Hassid et al, Noninvasive Magnetic Resonance Imaging of Transport of Interstitial Fluid Pressure in Ectopic Human Lung Tumors, Cancer Res 2006; 66 (8); Apr. 15, 2006, p. 4159-4166.

Dadiani et al, High-Resolution Magnetic Resonance Imaging of Dispartiies in the Transcapillary Transfer Rates in Orthotopically Innoculated Invasive Breast Tumors, Cancer Research, 64, p. 3144-61, May 1, 2004.

Rofstad et al, Pulmonary and Lymph Node Metastasis Is Associated with Primary Tumor Interstitial Fluid Pressure in Human Melanoma Xenografts, Cancer Research, 62, p. 661-664, Feb. 1, 2002.

Ansiaux et al, thalidomide Radiosensitizes Tumors through Early Changes in the Tumor Microenvironment, Clinical Cancer Research, vol. 11, p. 743-750, Jan. 15, 2005.

* cited by examiner

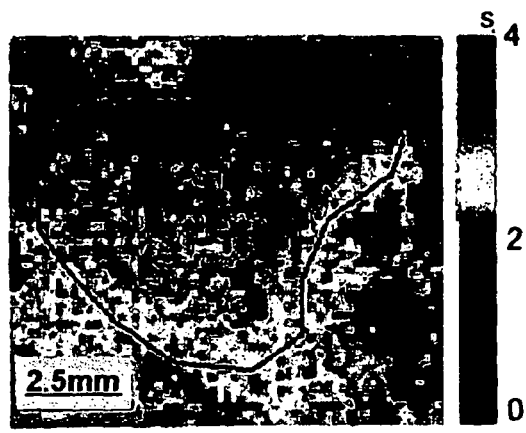 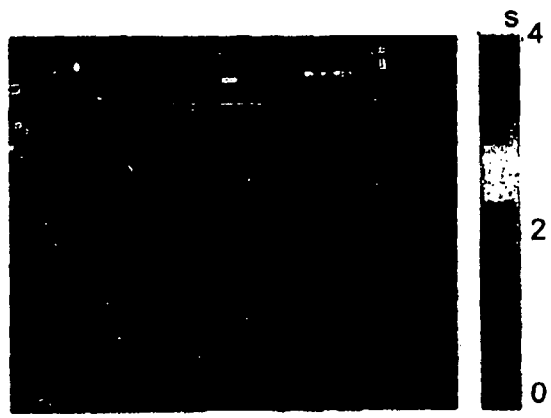
Fig. 4A  Fig. 4B
 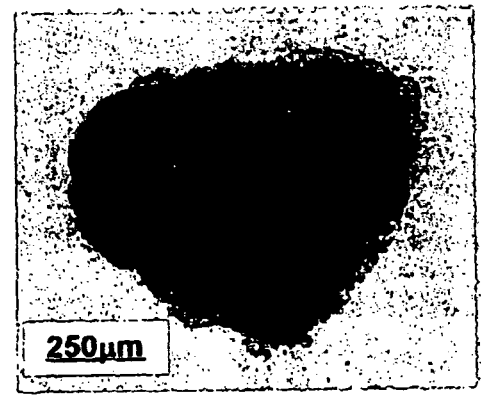
Fig. 4C  Fig. 4D

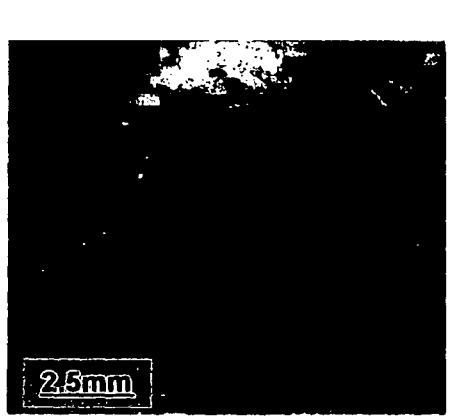
Fig. 5A  Fig. 5B
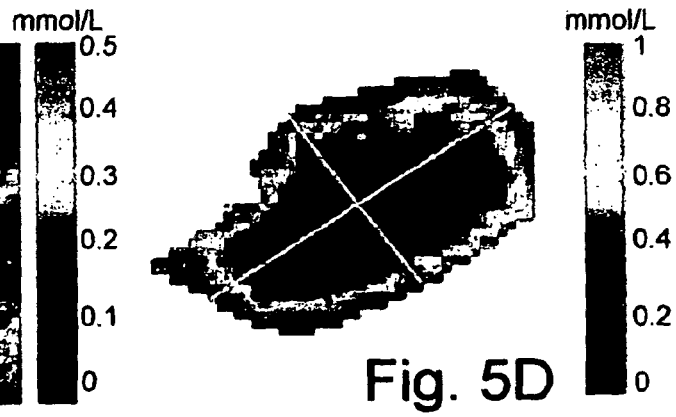
Fig. 5C  Fig. 5D
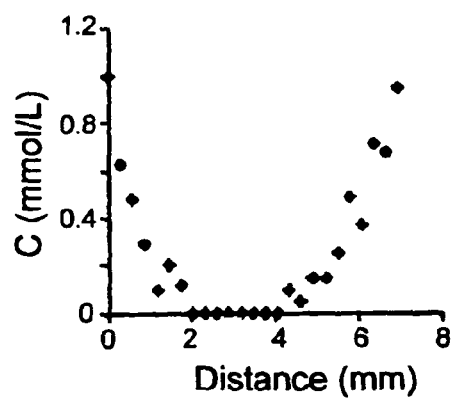
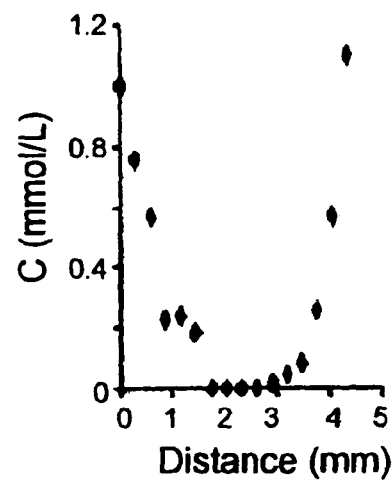
Fig. 5E  Fig. 5F

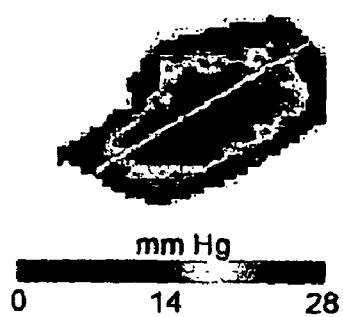 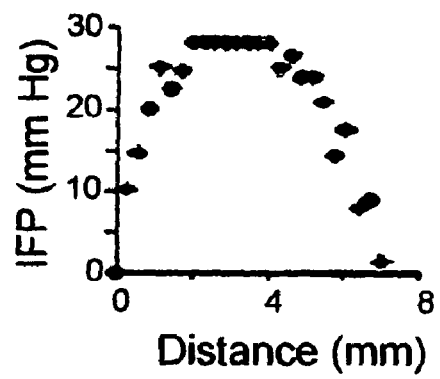
Fig. 7A
 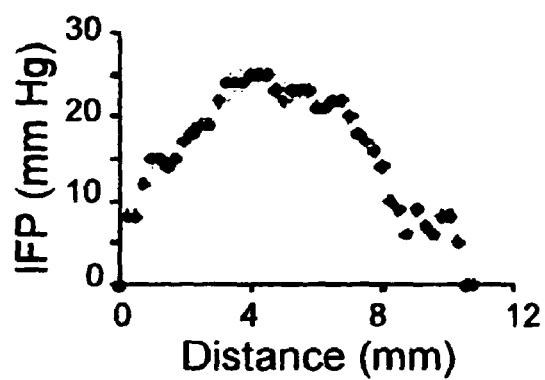
Fig. 7B
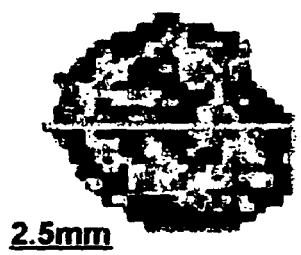 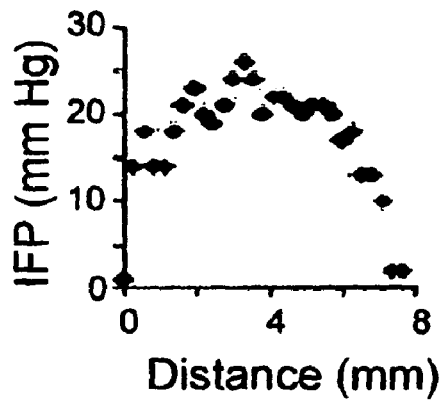
Fig. 7C

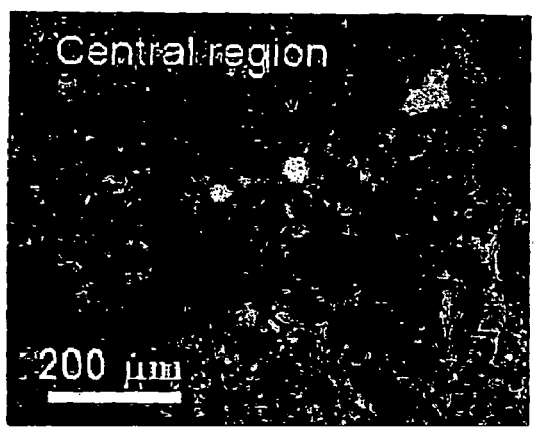
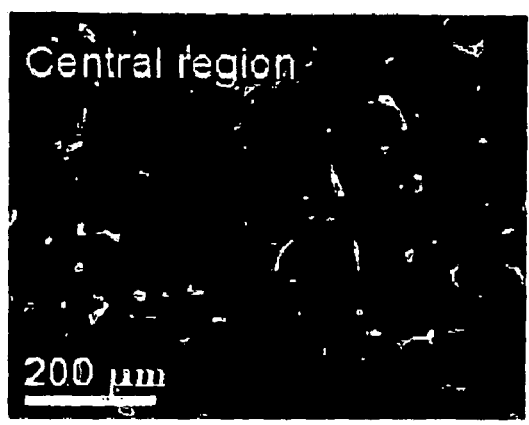
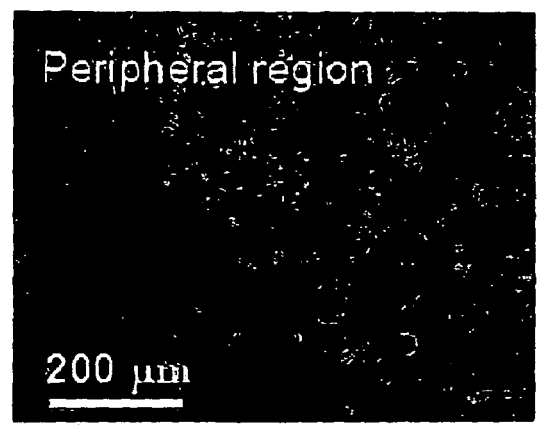
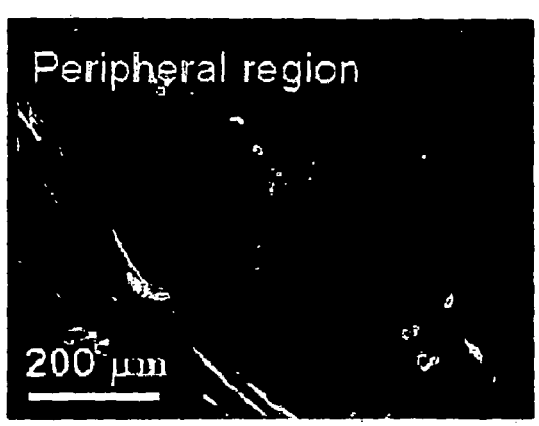
Fig. 10A          Fig. 10B

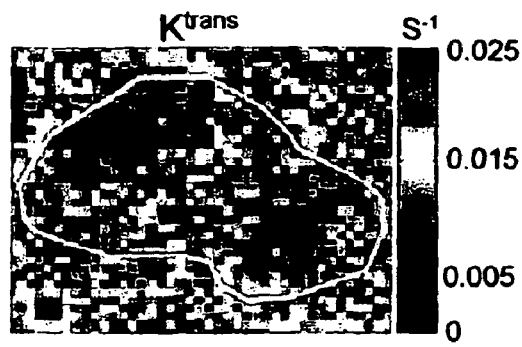
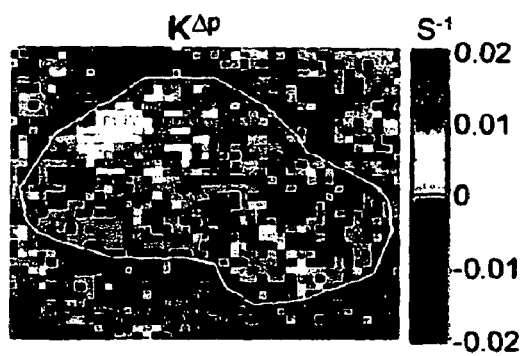
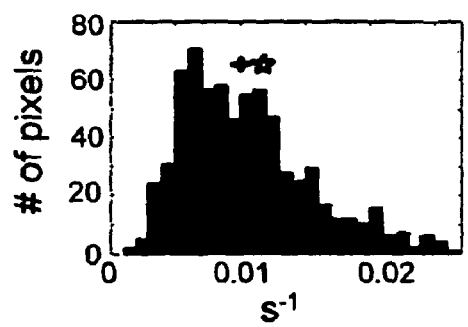
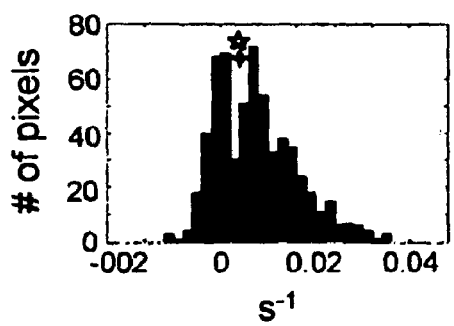
Fig. 12A          Fig. 12B
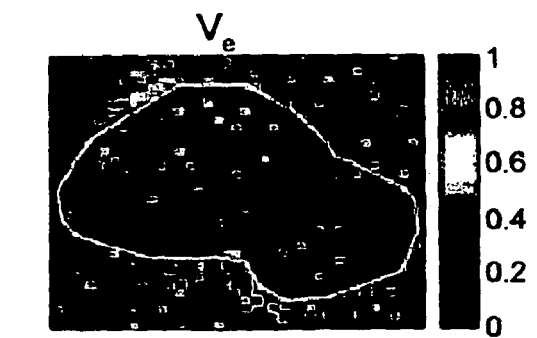
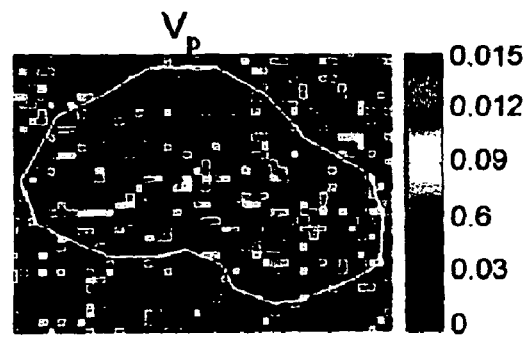
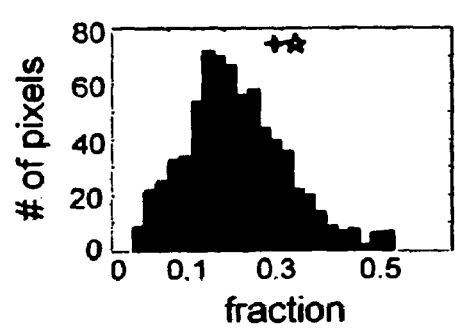
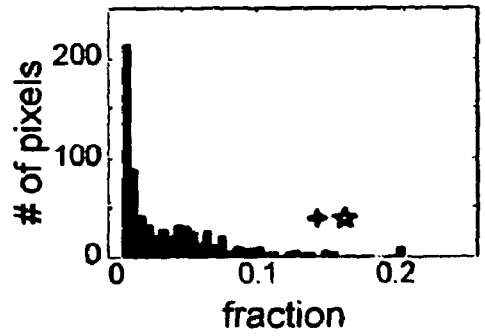
Fig. 12C          Fig. 12D

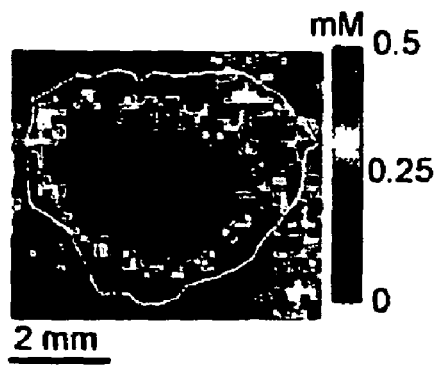
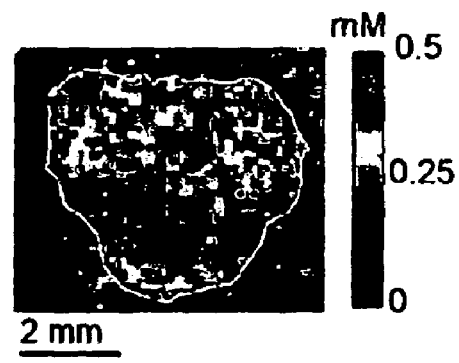
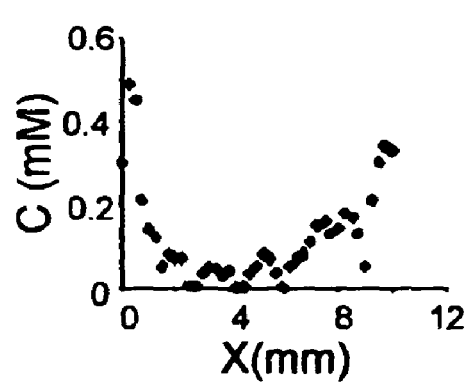
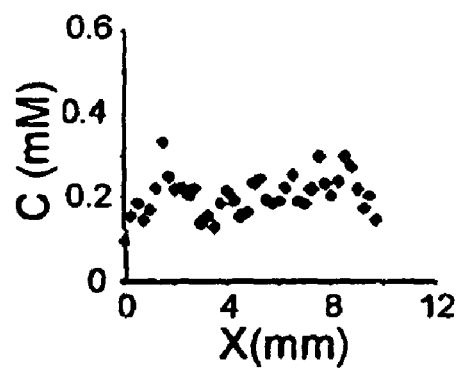
Fig. 14A                    Fig. 14B

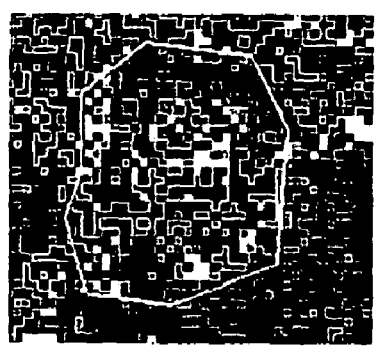 
Fig. 15A  Fig. 15B
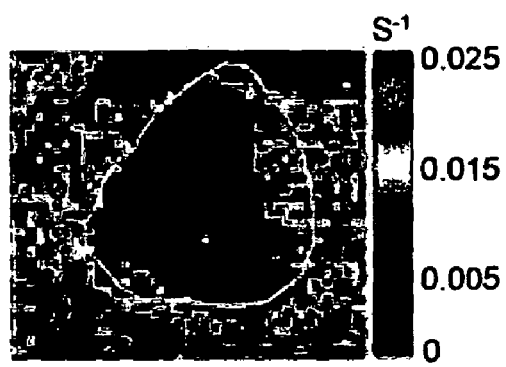 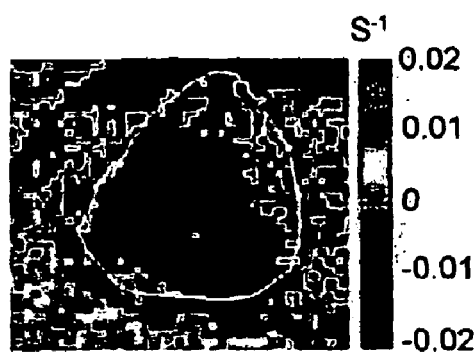
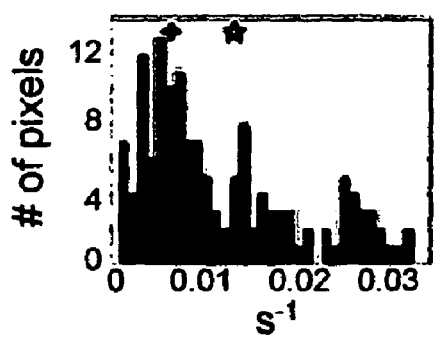 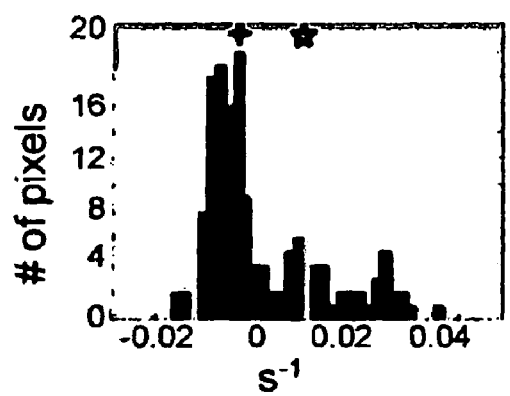
Fig. 16A  Fig. 16B

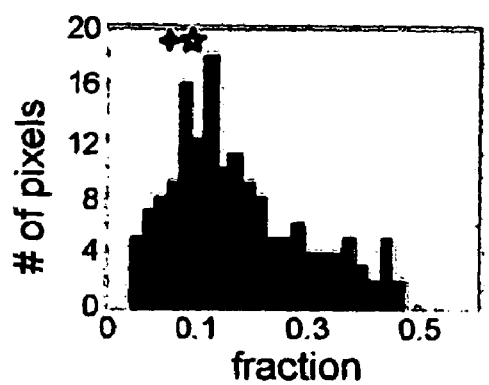
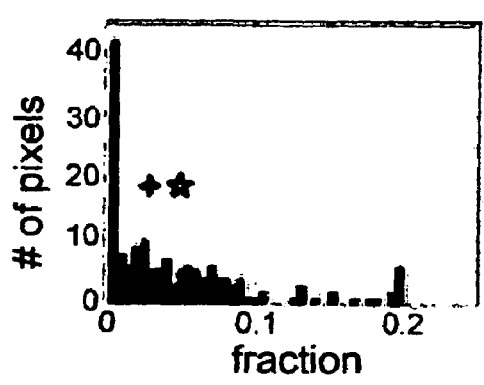
Fig. 16C    Fig. 16D
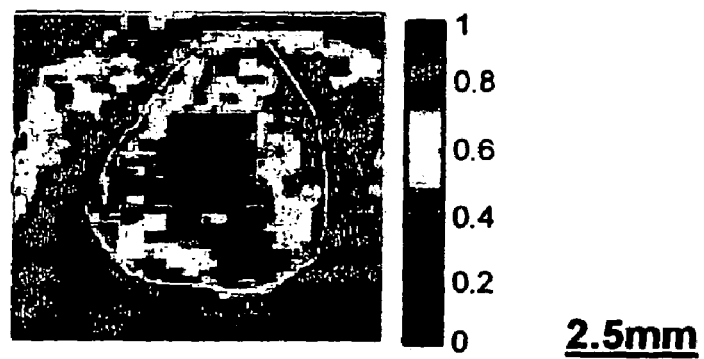
Fig. 16E

APPARATUS FOR MONITORING A SYSTEM PRESSURE IN SPACE WITH TIME AND METHOD FOR ASSESSING DRUG DELIVERY AND RESISTANCE TO THERAPY AND PRODUCT

CROSS-REFERENCE TO RELATED APPLICATIONS

This application is a U.S. National Stage application of International Application No. PCT/IL2007/001102, filed 6 Sep. 2007, which claims priority to U.S. Provisional application Patent No. 60/824,655, filed 6 Sep. 2006.

STATEMENT REGARDING FEDERALLY SPONSORED RESEARCH OR DEVELOPMENT

This invention was made with government support under CA 042238 awarded by the NIH. The government has certain rights in the invention.

BACKGROUND OF THE INVENTION

1. Field of the Invention

This invention relates to a method, apparatus and product for non-invasively monitoring an actual system pressure within a mammal in space with time; to a method, apparatus and product for non-invasively assessing drug delivery and resistance to therapy of a tumor or organ within a mammal; to non-invasively control and/or suppress or reduce pressure in a tumor or organ; and to a method, apparatus and product for non-invasively mapping delivery capacity by imaging actual interstitial fluid pressure and/or concentration or distribution of a tracer.

2. Prior Art

With respect to the physiology and clinical application, the majority of cancer diseases are managed with a variety of systemic therapeutic agents. These agents are usually administered through the blood circulation, enter the tumor vasculature, extravasate out into the tissue across the microvascular wall and move through the interstitial compartment into the cells overcoming the cells membrane barrier. However, these therapeutic agents may not reach the target cells because of high pressure gradients that do not allow entrance of the drug to the tumor. This inhibition of delivery of drugs is a form of a physical drug resistance and can drastically impair treatment of tumors. Thus, a recurring question in the treatment of malignant tumors has been whether treatment failure is due to inadequate delivery or ineffective drugs. To find out whether there is no barrier to delivery one requires a method that can map the delivery capacity by imaging the distribution of a tracer (or contrast agent) under specific conditions.

Water soluble low molecular weight contrast agents are usually administered into the blood circulation. Upon reaching the tumor vasculature they are transferred across the walls of the capillaries into the tumor interstitial compartment. Once in the interstitial compartment they either return to the blood capillaries or enter the lymphatic drainage system or move through the interstitium towards the tumors surroundings. Each of these processes involves transfer by diffusion in the direction of the concentration gradients, as well as transfer by filtration or convection in the direction of the pressure gradients.

Transport Across the Microvascular Wall

A blood-borne molecule that enters the vascular system of an organ or a tumor, reaches the cells in the tissue (or tumor) via: a. distribution through the vascular compartment; b. transport across the microvascular wall; and c. transport through the interstitial compartment. For a molecule of given properties each of these transport processes may involve convection (i.e. solute movement associated with bulk solvent movement related to pressure gradients) and diffusion (i.e. solute movement resulting from solute concentration gradients).

Thus the extravasation Js(g/s) of a blood borne tracer occurs by diffusion and convection according to equation 1 below.

$$Js = PS(Cp-Ci) + L_p \sigma[(PHv-PHi) - \sigma_T(Pv-Pi)] \qquad (1)$$

The first term describes the diffusion influence and the second term describes the pressure-convection influence. P (cm/s) is the vascular permeability coefficient, which is the proportionality constant that relates transluminal diffusion flux to concentration gradients. S (cm$^2$) is the vessel's surface area, Cp−Ci is the agent concentration difference between the plasma and the interstitial space (g/m), $L_p$ is the hydraulic conductivity which is the constant that relates fluid leakage to pressure gradients
PHv−PHi is the difference between vascular and interstitial hydrostatic pressure, σ (mmHg) is the osmotic reflection coefficient of the contrast agent which describes the effectiveness of the transluminal osmotic pressure difference in producing movement of the contrast agent across the vessel wall, $\sigma_T$ is the average reflection coefficient of the plasma proteins (s~1 for macromolecules and decreases towards zero as the molecular weight decreases) and Pv−Pi is the difference between the vascular and interstitial osmotic pressure.

Transport Through the Interstitial Space

Once a molecule has extravasated from the microcapillary to the interstitium, its movement through the interstitial space occurs by diffusion and convection. Equation 2 quantifies this process:

$$J_i = -D\frac{dC}{dx} - CR_F K \frac{dp}{dx} \qquad (2)$$

The first term describes the influence of the diffusion and the second term describes the influence of the convection on the movement of a molecule. D is the diffusion coefficient of the molecule in the interstitium, dC/dx is the concentration gradient, C is the molecule concentration, $R_F$ is its retardation factor, K is the tissue hydraulic conductivity for convective flow of water through the medium (K=k/v where k is Darcy's constant (hydraulic conductivity) and v is solvent viscosity) and dp/dx is the pressure gradient.

Jain and Baxter (1) derived the following partial differential equation that describes the changes with time in the contrast agent concentration in the extracellular-interstitial fraction $$\frac{\partial C_i}{\partial t}$$

for a spherical tumor with a radius r.

$$\frac{\partial C_i}{\partial t} = \frac{D}{r^2}\frac{\partial}{\partial r}\left(r^2\frac{\partial C_i}{\partial r}\right) - r_f \frac{1}{r^2}\frac{\partial}{\partial r}\left(r^2 K \frac{dp_i}{dr} C_i\right) + + \frac{PS}{V}(C_p - C_i)Pl_v/(e^{Plv}-1) + \frac{L_p S}{V}(1-\sigma)[(p_v - p_i - \sigma_T(\pi_v - \pi_i)]C_p \qquad (1)$$

The first term on the right hand side is related to diffusion in the interstitial space which is determined by the tracer diffusion rate in the interstitial space D in units of cm²/s, the radial position in the tumor, r, and, the concentration gradient in the interstitial space $$\frac{\partial C_i}{\partial r}.$$

The second term describes the convection of the contrast agent in the interstitial space, which is determined by the retardation factor of the tracer, $r_f$, the radial position in the tumor, the hydraulic conductivity of the interstitial fluid, K in units of cm²/mmHg·s and the pressure gradient in the interstitial space $$\frac{\partial p_i}{\partial r}.$$

The third term reflects the diffusion due to concentration gradients across the capillary walls and is determined by the capillary permeability multiplied by the capillary surface area per unit volume PSN in units of s⁻¹, the transcapillary concentration difference between the plasma and the interstitial compartment (Cp−Ci), and the Peclet number ($P_{i,v}$)—the ratio of convection to diffusion through the capillary wall.

The fourth term reflects the transfer due to pressure gradient across the capillary walls and is determined by the hydraulic conductivity of the capillary multiplied by the capillary surface area per unit volume LpS/V in units of (mmHg·s⁻¹), the reflection coefficient of the contrast agent σ, The pressure difference between the intravascular and the interstitial spaces, ($p_v$−$p_e$), as well as by the average reflection coefficient of the plasma proteins, $v_T$, multiplied by the osmotic pressure gradients between the plasma (vv) and the interstitial space (πi).

Theoretically it is possible to solve equation (1) under special boundary conditions and then fit a time course of the interstitial concentration to this equation. However, there are 10 free parameters that are unknown and hence, it is impractical to extract these parameters from a single time course. By using certain assumptions and approximations it is possible, however, to simplify the equation, and reduce the number of unknown parameters thereby make it possible to quantify the transfer properties of the contrast agent into and out from a tumor.

The first step in the simplification process is based on the assumption that the tumor can be divided into two regions a) a region in which the interstitial fluid pressure (IFP) is low and positive pressure gradients from the capillaries outwards favor extravasation of the contrast agent and b) a region in which IFP is high and the positive transcapillary pressure gradients are cancelled and replaced by negative gradients, which by convective transfer move the contrast agent in the interstitium to low IFP regions inside or outside the tumor. In both regions we also neglect the concentration dependent diffusion of the contrast agent in the tumor's interstitial space assuming that the exchange across the capillary walls by the concentration gradient is predominant.

The motion of the contrast agent in region (a) with low or negative IFP is determined by a diffusive transcapillary transfer constant $$\frac{PS}{V} Pl_v / (e^{Plv} - 1)$$

defined as $k^{trans}$, and a pressure dependent transcapillary extravasation constant $$\frac{L_p S}{V}(1-\sigma)[(p_v - p_i - \sigma_T(\pi_v - \pi_i)]$$

defined as $k^{\Delta p}$ and hence, the change in the concentration of the contrast agent in the interstitial compartment is given by $$\frac{dC_i}{dt} = k^{\Delta p} C_p + k^{trans}(C_p - C_i) \qquad (2)$$

In order to solve this equation it is necessary to know the time dependent changes in the concentration of the contrast agent in the plasma (Cp(t)). For an instantaneous, bolus administration of the contrast agent this time course can be given by a biexponential decay (2) according to:

$$C_p(t) = D_s(a_1 e^{-m_1 t} + a_2 e^{-m_2 t}) \qquad (3)$$

where Ds is the dose, $a_1$ $a_2$ are the amplitude of the components and $m_1$ $m_2$ are their rate constants (2).

Using a MRI contrast agent requires taking into account the fact that the MRI reflects the total amount of spins per voxel volume, Ct (assuming fast exchange of the water between the intra to extravascular compartments) rather than the amount per interstitial volume, namely the interstitial concentration (2) and therefore Ct=$v_e$×Ci where $v_e$ is the extracellular volume fraction. The solution of 2 and 3 for Ct is therefore:

$$C_t(t) = (k^{trans} + k^{\Delta p}) D \sum_{i=1}^{2} \frac{a_i \left(e^{-\frac{k^{trans}}{v_e}t} - e^{-m_i t}\right)}{m_i - \frac{k^{trans}}{v_e}} \qquad (4)$$

The tumor tissue includes also the intravascular volume. Usually the intravascular volume fraction is low and can be neglected, but it is possible to add a term that describes the contrast agent concentration in this volume yielding the total tissue concentration of the contrast agent per unit volume of tissue.

$$C_t(t) = (k^{trans} + k^{\Delta p}) D \sum_{i=1}^{2} \frac{a_i \left(e^{-\frac{k^{trans}}{v_e}t} - e^{-m_i t}\right)}{m_i - \frac{k^{trans}}{v_e}} + v_p D \sum_{i=1}^{2} a_i e^{-m_i t} \qquad (5)$$

where $v_p$ is the vascular volume fraction.

It is also possible to inject the contrast agent by slow infusion at a constant rate. For an i.v. infusion rate $D^{inf}$ starting at time t=0, this injection can be treated as a series of small doses $\Delta D = D^{inf} \Delta t'$, each lasting time $\Delta t'$. The plasma concentration $$C_p^{inf}(t) = \lim_{\Delta t' \to 0} \sum_{t'=0}^{t} \Delta C_p(t) = D^{inf} \sum_{i=1}^{2} \frac{a_i(1-e^{m_i t})}{m_i} \qquad (6)$$

is the sum of the contributions from each doselet (3):

Thus for slow infusion the solution of Equation (2) using Equation (6) and adding the contribution of the vascular volume yields:

$$C_t(t) = D_{inf}(k^{trans} + k^{\Delta P}) \tag{7}$$

$$\sum_{i=1}^{2} a_i \left( \frac{1 - e^{-\left(\frac{k^{trans}}{v_e}\right)t}}{\frac{k^{trans}}{v_e}} - \frac{1 - e^{-m_i t}}{m_i} \right) \bigg/ \left( m_i - \frac{k^{trans}}{v_e} \right) + +$$

$$v_p D_{inf} \sum_{i=1}^{2} a_i \left( \frac{1 - e^{-m_i t}}{m_i} \right)$$

The motion of a contrast agent in region (b) with high IFP is mainly determined by the diffusive transcapillary transfer and by pressure gradient dependent convective transfer in the interstitial volume. The convective transfer decreases the contrast agent concentration in these regions. The differential equation describing the change in the contrast agent concentration in these regions is: ($k^{\Delta p}$ has a negative sign)

$$\frac{dC_i}{dt} = -k^{\Delta p} C_i + k^{trans}(C_p - C_i) \tag{8}$$

Where $$k^{\Delta P} = r_f \frac{1}{r^2} \frac{\partial}{\partial r}\left( r^2 K \frac{dp_i}{dr} \right)$$

and $$k^{trans} = \frac{PS}{V} Pl_v / (e^{Pl_v} - 1)$$

This differential equation, which includes space dependent and time dependent parameters, has no analytical solution. We therefore approximated the convective motion neglecting the space dependent component in Equation (8) and assuming that in all the pixels of this region (usually the inner parts of solid tumors) this term is similar, and hence $k^{\Delta p}=rfK(\Delta p)$, where $\Delta p$ is the pressure difference that causes convection from a voxel of high IFP to a voxel of low IFP. With this approximated $k^{\Delta p}$ Equation (8) becomes a solvable first order differential equation. The solution of (8) (after conversion to Ct) for a bolus injection of the contrast agent, using Equation (3) and, including the contribution of the intravascular volume fraction is:

$$C_t(t) = k^{trans} D \sum_{i=1}^{2} \frac{a_i \left( e^{-\left(\frac{k^{trans}+k^{\Delta p}}{v_e}\right)t} - e^{-m_i t} \right)}{m_i - \left(\frac{k^{trans}+k^{\Delta p}}{v_e}\right)} + v_p D \sum_{i=1}^{2} e^{-m_i t} \tag{9}$$

For administration of the contrast agent at a slow infusion rate the solution is:

$$C_t(t) = D_{inf} k^{trans} \tag{10}$$

$$\sum_{i=1}^{2} a_i \left( \frac{1 - e^{-\left(\frac{k^{\Delta P}+k^{trans}}{v_e}\right)t}}{\frac{k^{\Delta P}+k^{trans}}{v_e}} - \frac{1 - e^{-m_i t}}{m_i} \right) \bigg/ \left( m_i - \frac{k^{\Delta P}+k^{trans}}{v_e} \right) + +$$

$$v_p D_{inf} \sum_{i=1}^{2} a_i \left( \frac{1 - e^{-m_i t}}{m_i} \right)$$

In summary, approximated equations have been developed for the time dependent changes in the concentration of a contrast agent in tissues, specifically tumors. These equations that take into account concentration gradients across the capillary walls that lead to diffusive transcapillary transfer, pressure dependent gradients across the capillary walls that lead to filtrative (or extravasative) transcapillary transfer and pressure gradients within the interstitial compartment that lead to convective transfer within the interstitium from high IFP to low IFP.

In the case of a bolus injection of the contrast agent, in order to determine whether a voxel belongs to region (a) with low IFP or region (b) with high IFP, the MRI derived enhancement curves can be fitted to Equation 5 and Equation 9. The better fitting (assessed for example by calculating the higher value of proportion of variability, $R^2$) provides a means to select the type of region ((a) or (b)) and the corresponding transfer constants.

In the case of slow infusion of the contrast agent, in order to determine whether a voxel belongs to region (a) with low IFP or region (b) with high IFP, the MRI derived enhancement curves can be fitted to Equation 7 and Equation 10, the better fitting ((a) or (b)) and the corresponding transfer constants.

Because the drop in the plasma concentration after a bolus injection is very fast, in parts of tumors' regions it is difficult to detect a transfer of constant agent (low or null enhancement). However, it is not clear whether the low or null transfer is due to low concentration dependent diffusive transfer across the capillary walls or to high IFP in the interstitium and outward convection. In contrast, when a slow infusion is used, the plasma concentration is continuously increasing reaching a maximum value at steady state (steady state is defined as the state when the rate of injection is equals the rate of clearance through the kidneys into the urine and hence the plasma concentration is constant). Hence, even if the concentration dependent diffusive transfer across the capillary walls is low the interstitium will be filled up at steady state and the low transfer constant can be determined. If, however there is no or low enhancement at steady state it is clear that the IFP is high in this region. Thus, the slow infusion enables determining the mechanism of contrast agent transfer ((a) or (b)) even when the diffusive transfer constant is low.

Interstitial Fluid Pressure (IFP)

Interstitial fluid pressure is the hydrostatic pressure of water in the extracellular extravascular compartment measured in mmHg. Normal tissues possess interstitial fluid pressure of (−2)-0 mmHg, while tumors often possess higher Interstitial Fluid Pressure of 10-50 mmHg. IFP in Tumors reaches high values due to:

1. The proliferation of cells in a confined area
2. High water permeability of the vascular wall
3. Lack of functioning lymphatic vessels and drainage of water.
4. Metabolic induced increase in IFP: The main metabolic event is enhanced glycolysis that produces two lactate molecules from one glucose molecule. Lacate molecules usually accumulate in the interstitial space, and thereby increase osmotic pressure.
5. Composition of the interstitial compartment which determines the interstitium elasticity and the interstitial fibers contractility and flexibility.

In the prior art it has been suggested that in the center of tumors interstitial fluid pressure (IFP) can exceed the vascular blood pressure while in the periphery it is lower than the vascular blood pressure. Consequently molecules mainly extravasate from blood vessels in the tumor periphery. Elevated interstitial fluid pressure changes the movement of molecules through the compartments leading to restrict accumulation of therapeutic agents in the tumors. Namely, elevated interstitial fluid pressure attenuates extravasation of drugs from capillaries to central regions of tumors, and creates convection of the drug from the tumor center outward, in the direction of the interstitial pressure gradient.

Modulation of Pressure Balance by Drugs

Few attempts were made in order to elevate drug concentration in tumors that exhibit high IFP. The strategy was to apply pharmaceutical agents that influence blood pressure and flow in order to increase extravasation to tumor tissues; however these studies were not aimed at improving delivery by reducing interstitial pressure.

Most of the experiments were performed on rodents bearing implanted tumor xenografts. Drugs of three major pharmaceutical groups were applied: vasoconstrictors, vasodilators and drugs that reduce blood viscosity.

IFP Measuring Methods

Currently, there are two main methods for measuring interstitial fluid pressure, Perforated capsule and Needle methods. These methods are not imaging methods and can measure pressure in limited loci in a tumor. The notable disadvantage of these methods is their invasiveness, which results in damaging the investigated tissue including elevating its interstitial fluid pressure. Furthermore, these methods cannot be used in internal organs and tumors.

Perforated Capsule (Micropore Chamber) Method

The capsule method employs a porous polyethylene capsule surgically implanted in the tissue to be studied. After several weeks, the fluid in the capsule reaches equilibrium with the surrounding interstitial fluid. The pressure of the fluid within the capsule is then measured with a pressure transducer. This method has the following disadvantages: 1. Surgical implantation is required and a prolonged period for equilibration. 2. The observed pressure is influenced by the osmotic gradient between the fluid inside and the fluid outside the capsule. 3. Implantation of the capsule can cause immune response, which changes the pressure of the tissue.

Wick in Needle Method

The wick-in-needle technique consists of a hypodermic needle connected to a pressure transducer via tubing filled with saline. The needle is then placed in the tumor where the pressure is to be measured. The needle hole is filled with polyester or other fiber to improve the fluid communication between the probe and the tumor tissue. The pressure is increased until fluid flows into the tissue. The pressure at this point is considered to be equal to the interstitial fluid pressure. The pressure transducer converts the pressure to a voltage, which is logged by a computer. This method has some drawbacks: It can cause tissue distortion and trauma, as well as increase interstitial fluid pressure. Micropipettes and servo null device were used in order to overcome these disadvantages.

In a published article (4) it was reported that tumor response to blood borne drugs is critically dependent on the efficiency of vascular delivery and transcapillary transfer. However, increased tumor interstitial fluid pressure (IFP) forms a barrier to transcapillary transfer, leading to resistance to drug delivery. Presented was a new, noninvasive method which estimated IFP and its spatial distribution in vivo using contrast-enhanced magnetic resonance imaging (MRI). The method was tested in ectopic human non-small-cell lung cancer which exhibited a high IFP of ~28 mm Hg and, for comparison, in orthotopic MCF7 human breast tumors which exhibited a lower IFP of ~14 mm Hg, both implanted in nude mice. The MRI protocol consisted of slow infusion of the contrast agent [gadolinium-diethylenetriaminepentaacetic acid (GdDTPA)] into the blood for ~2 hours, sequential acquisition of images before and during the infusion, and measurements of T1 relaxation rates before infusion and after blood and tumor GdDTPA concentration reached a steady state. Image analysis yielded parametric images of steady-state tissue GdDTPA concentration with high values of this concentration outside the tumor boundaries, ~1 mmol/L, declining in the tumor periphery to ~0.5 mmol/L, and then steeply decreasing to low or null values. The distribution of steady-state tissue GdDTPA concentration reflected the distribution of IFP, showing an increase from the rim inward, with a high IFP plateau inside the tumor. The changes outside the borders of the tumors with high IFP were indicative of convective transport through the interstitium. The article presented a noninvasive method for estimating and based thereon assessing the spatial distribution of tumor IFP and mapping barriers to drug delivery and transport. The main disadvantage of this proposed method is that it results in an estimate only.

The main drawback of the prior art is the inability to determine actual interstitial fluid pressure non-invasively.

SUMMARY OF THE INVENTION

The present invention presents a method, apparatus and a computer readable medium containing executable instructions for monitoring a system pressure within a mammal, human or animal, in space in time for determining non-invasively actual interstitial fluid pressure. Further, the invention provides an imaging method, an apparatus and a product for non-invasive mapping of interstitial fluid pressure. Still further, the present invention provides a non-invasive method, apparatus and product for assessing drug delivery and resistance to therapy of a tumor or organ within a mammal, and to a method and apparatus for mapping delivery capacity by imaging distribution of a tracer. The invention further provides a computer readable medium containing executable instructions for conducting mapping of interstitial fluid pressure, and to control the delivery of drugs to tumors.

The foregoing is accomplished by a method and apparatus and computer readable medium that contains executable instruction whereby a contrast agent is administered by a slow contrast agent infusion into the blood circulation of the mammal while monitoring by MRI the concomitant changes in signal enhancement, and processing according to a novel algorithm in order to determine non-invasively actual interstitial fluid pressure in a tumor or organ or any other tissue in a human or animal.

For example it is possible to infuse the regular dose used regularly for a bolus injection (0.1 to 0.2 mmol/Kg weight for humans and 0.1-0.4 mmol/Kg wt for rodents) over the period of infusion. Hence for 30 min slow infusion the rate of infusion would be (0.0033 to 0.0066 mmol/min/Kg wt for humans) for 60 min slow infusion the rate would be twice slower. Similarly, in rodents, the rates of infusion can be in the same range as for humans or twice faster than in humans.

After a determined time from the start of the infusion, as monitored by and indicated by the MRI, the concentration of the contrast agent in the blood circulation reaches a steady state, i.e., the rate of infusion becomes equal to the rate of clearance from the blood through the kidneys into the urine. Following blood steady state, other parts of the mammal also reach steady state concentration. the monitoring by MRI both before and during slow infusion of the contrast agent produces output images indicative of changes in contrast agent concentration in the system that are processed according to a novel algorithm to obtain data regarding transfer constants and values of pressure gradients, and to obtain data regarding the differences in space between the distribution of the tracer due to the presence of pressure gradients; from the determined data mapping the pressure gradients to obtain an output thereof. Essentially, the invention can determine and monitor interstitial fluid pressure (IFP) in an ongoing basis, so that the effective transcapillary transfer or transport through the interstitium from adjacent regions is known, in turn, giving an indication of delivery of or resistance to delivery of a drug to a tumor or organ.

In a further refinement of the invention, the determination of the pressure gradients can be employed to monitor simultaneously the delivery of drugs to a tumor or organ and/or the resistance to delivery of drugs to a tumor or organ. In a still further refinement of the invention, the determination of pressure gradients in the interstitium can be employed to monitor simultaneously the delivery of drugs to a tumor or organ and/or the resistance to delivery of drugs to a tumor or organ, and to indicate the administration of an ancillary drug to lower the pressure inside a tumor or organ to enable the drug being administered to enter the tumor or organ.

Other and further objects and advantages of the present invention will become more readily apparent form the following detailed description of the invention when taken in conjunction with the appended drawings.

BRIEF DESCRIPTION OF THE DRAWINGS

FIG. 4A to 4D shows parametric images of $T_1$ relaxation times and calculated tissue GdDTPA concentration at steady state of an ectopic H460 tumor.

FIG. 5A to F show parametric images of $T_1$ relaxation limes and calculated GdDTPA concentration maps and profiles at steady state of an ectopic H460 tumor.

FIG. 7 show estimated IFP maps and profiles of typical ectopic H460 tumors.

FIG. 10 illustrates histopatholgy and blood capillaries in NSCLC H460 tumors implanted in the flank of nude mice; FIG. 10A shows hematoxylin and eosin staining of a central region and a peripheral region of a tumor and FIG. 10B shows CD31 immunostaining of the blood capillaries a in a central and a peripheral region of the tumor in A.

FIG. 11 illustrates maps of steady-state tissue GdDTPA concentration in H460 tumors.

(a, b, and c) maps of positive and negative pressure gradients dependent transfer constant (+/−$k^{\Delta p}$) and steady state interstitial GdDTPA concentration in a typical tumor, and the Pearson correlation of these two parameters in the tumor ROI (r=0.72; p<0.00001), respectively; (c, d, and e) maps of +/−$k^{\Delta p}$ and steady state interstitial GdDTPA concentration in a second typical tumor, and the Pearson correlation of these two parameters in the tumor ROI (r=0.72; p<0.00001), respectively; the boundary of each tumor, marked in white, was initially outlined on the $T_2$ weighted image and transferred to the corresponding maps of the vascular parameters.

FIG. 14 shows collagenase induced changes in the steady-state tissue GdDTPA concentration of H460 tumors; a and c. map and profile of the steady state tissue GdDTPA concentration 24 hours before the administration of collagenase (0.4 mg/kg body w); b and d map and profile of the steady state tissue GdDTPA concentration 5 hours after the i.v. administration of collagenase to the tumor in a; maps were calculated from $T_1$ relaxation rates measured before and during infusion of GdDTPA, when it reached steady state.

FIG. 15 show +/−$k^{\Delta p}$ 24 h before treatment with collagenase (a) and 5 h after treatment with collagenase; (b) the maps were calculated from the dynamic pattern during slow infusion.

Note the increase in $k^{\Delta p}$ in the center of the tumor due to reduced IFP and the decrease of accumulation of contrast agent in the tumor surrounding.

Figure 12E:
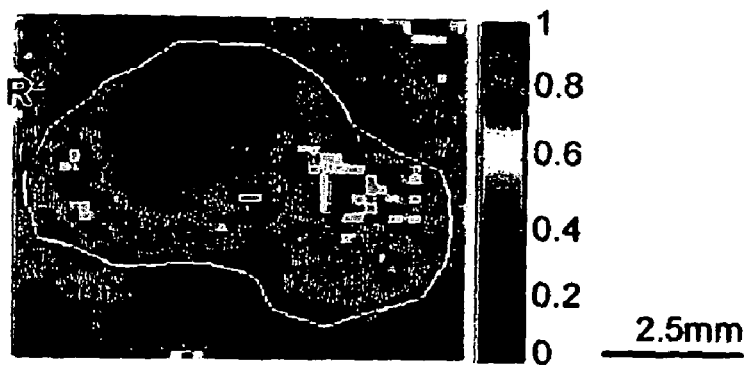
FIG. 12 shows maps and frequency distribution of the vascular parameters in a tumor in which the contrast agent reached all areas; the parameters were calculated from DCE-MR images scanned during GdDTPA infusion; IFP inside this tumor was 26 mm Hg; a) Concentration gradients dependent transcapillary transfer constant ($k^{trans}$) map; b) positive and negative pressure gradients dependent transfer constant (+/−$k^{\Delta p}$) map; c) extracellular extravascular volume fraction ($v_e$) map; d) iIntravascular volume fraction ($v_p$) map; e) proportion of variability ($R^2$) map presents best fit to extravasation or convection behavior; the median position of each parameter is marked by a +, and the mean by a *; The boundary of each tumor, marked in white, was initially outlined on the $T_2$ weighted image and transferred to the corresponding maps of the vascular parameters.
Figure 13A:
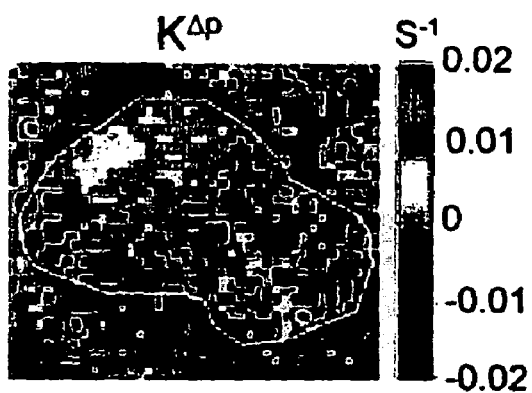
FIG. 13 shows correlation of +/−$k^{\Delta p}$ and steady state interstitial GdDTPA concentration maps.
Figure 13D:
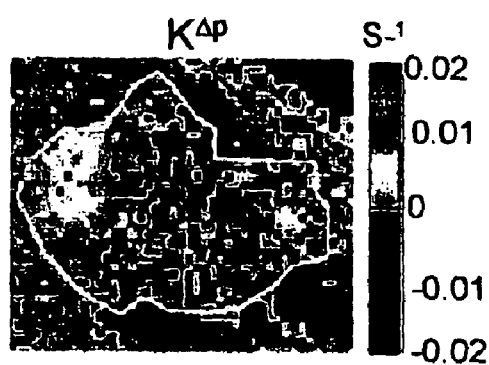
Figure 13B:
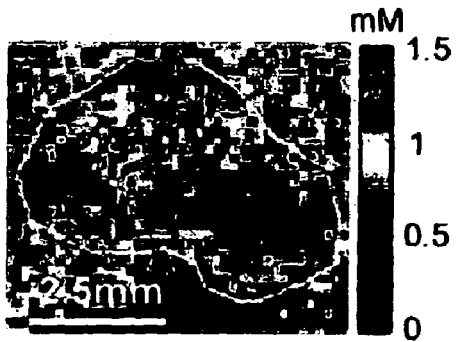
Figure 13E:
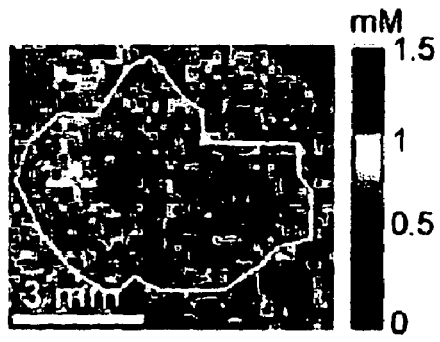
Figure 13C:
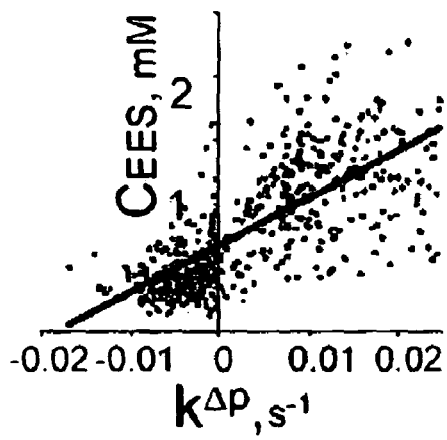
Figure 13F:
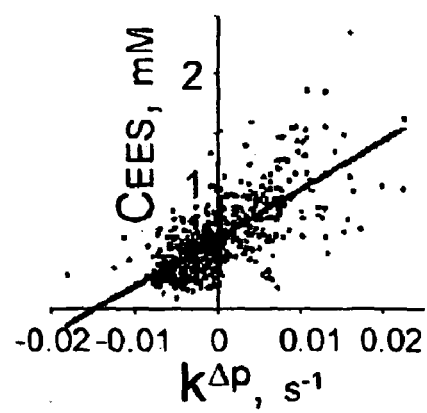
Figure 13H:
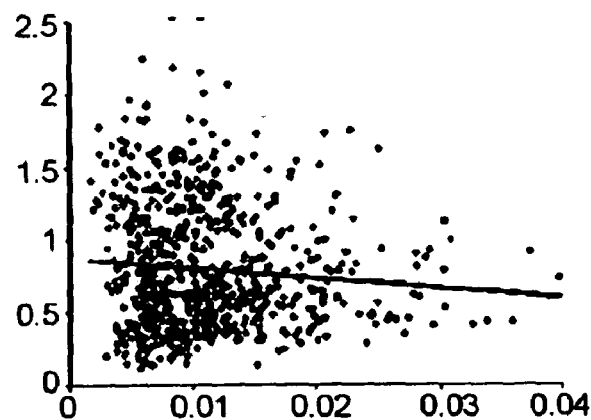
Figure 13G:
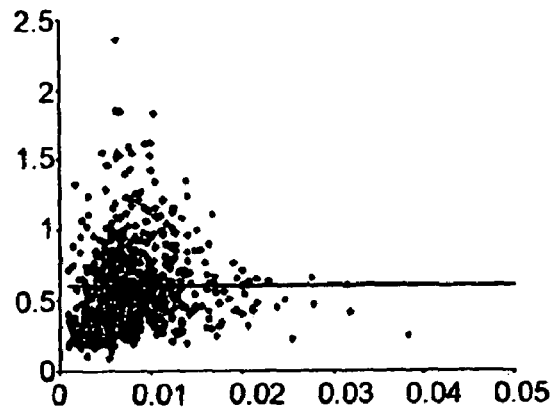

FIG. 16 shows an example of the analysis of dynamic curves during slow infusion for a tumor with high IFP and null entrance of contrast agent at steady state as in FIG. 12.

DETAILED DESCRIPTION OF PREFERRED EMBODIMENTS OF THE PRESENT INVENTION

The method and apparatus of the present invention will now be described. Described is an imaging method and apparatus for non-invasive mapping of interstitial fluid pressure in a subject or part of a subject. The subject under consideration can be a mammal, an animal or human, but more particularly, a tumor or organ in a body and the volume immediately surrounding. In a specific embodiment of the invention, the imaging is with respect to a tumor or organ in a body and the volume immediately surrounding.

Figure 9:
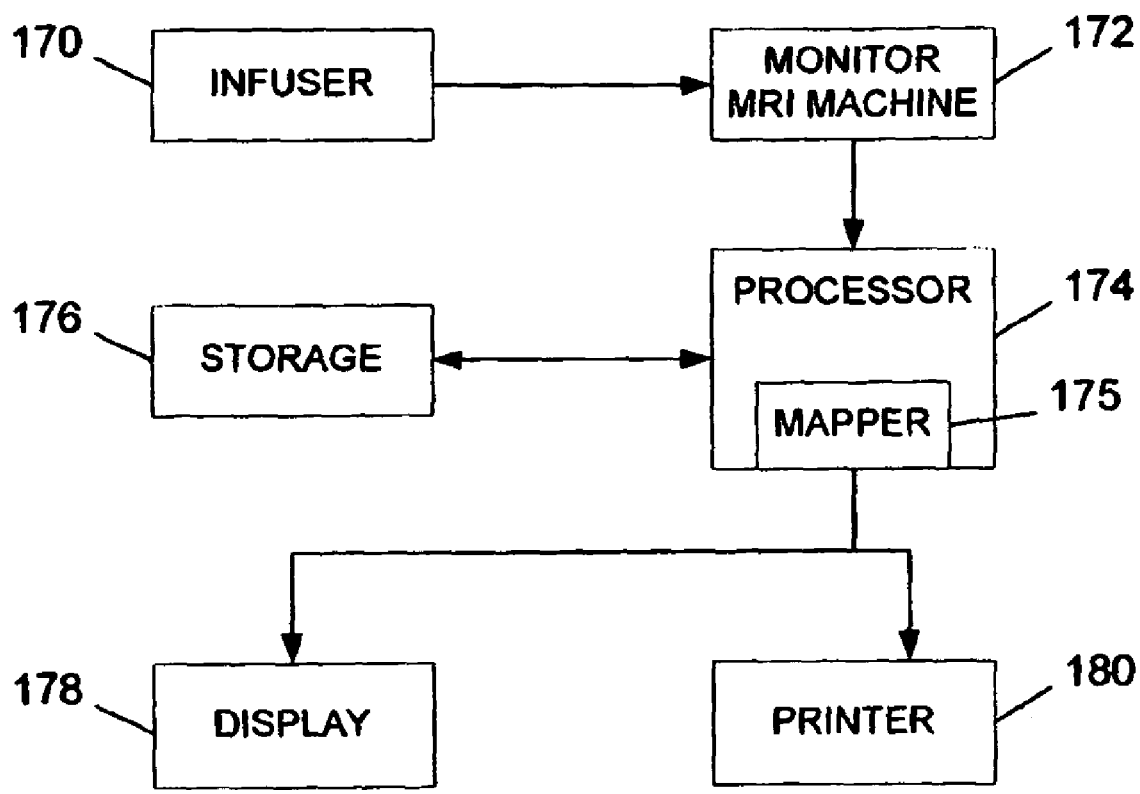
FIG. 9 is a block diagram showing generally the apparatus of the invention.

The apparatus is shown generally in FIG. 9 and consists of an infuser 170 coupled to signal a monitor 172, which preferably is an MRI machine. The output images of the monitor 172 are sent to a processor 174 and to storage 176. The processor processes the MRI images as will be explained in detail hereafter and sends the processed images to an included mapper 175 that outputs the processed images in colored map form with the color and intensity correlated with the resulting processed images, and the mapper 175 output is sent to one or more of the storage 176, a display 178 and a printer 180.

The invention, in one form, is an apparatus for non-invasive mapping of interstitial fluid pressure in a mammal in space with time of a preselected location comprising: (a) an infuser for infusing a tracer/contrast-agent into a mammal that flows throughout the mammal, as well as, clears out from the mammal; (b) a monitor for monitoring a preselected location in a mammal for collecting data indicative of changes in tracer concentration with time and providing a first output; (c) a data processor including first circuitry responsive to the first output of the monitor for receiving the collected data and processing same to obtain transfer constants and pressure gradients characteristic of the preselected location and providing a second output; (d) said data processor including second circuitry for determining from the first and second outputs tracer concentration at steady state and the differences in space between the distribution of the tracer due to the presence of pressure gradients and providing a third output; and (e) a mapper for receiving the second and third outputs and mapping pressure gradients in the preselected location for determining the efficacy of drug delivery to the selected location and generating a fourth output.

In the apparatus described above, the monitor is preferably an MRI system. Also, one of (i) a display is provided to receive the fourth output and display the resultant map, (ii) storage is provided to store the resultant map, and (iii) a printer is provided to receive the fourth output and print the resultant map. Still further, the apparatus can be provided with a means to control drug delivery responsive to the fourth output.

The invention further comprises a computer readable medium having computer executable program code thereon including: first program logic for monitoring a preselected location in a mammal for collecting data indicative of changes in tracer concentration with time and providing a first output; second program logic responsive to the first program logic for receiving collected data and processing same to obtain transfer constants and pressure gradients characteristic of the preselected location and providing a second output; third program logic responsive to the first and second program logic for determining tracer concentration at steady state and the differences in space between the distribution of the tracer due to the presence of pressure gradients and providing a third output; and fourth program logic responsive to the second and third program logic for deriving a fourth output indicative of pressure gradients in the preselected location that, in turn, are indicative of the efficacy of drug delivery to the selected location.

The computer readable medium as described above can include a fifth program logic responsive to the fourth program logic for mapping the fourth output, and providing a fifth output to be displayed. Also, the computer readable medium can include a further program logic responsive to the fourth program logic for providing a control of a drug delivery system to the preselected location.

In another form of the invention, a data processing system is provided for non-invasive determining interstitial fluid pressure in a mammal, human or animal, in space with time of a preselected location comprising: (a) data storage; (b) a first processor controller for slowly infusing a tracer/contrast-agent into a mammal that flows throughout the mammal, as well as, clears out from the mammal; (c) a second processor controller for monitoring a preselected location in a mammal for collecting data indicative of changes in tracer concentration with time and providing a first data output that is stored in the data storage; (d) a third processor controller including first circuitry responsive to the first data output of the monitoring and processing same to obtain transfer constants and pressure gradients characteristic of the preselected location and providing a second data output; (e) a fourth processor controller including second circuitry for determining from the first data output tracer concentration at steady state and the differences in space between the distribution of the tracer due to the presence of pressure gradients and providing a third data output; and (f) a fifth processor controller for receiving and processing the second and third data outputs to provide a fourth data output indicative of pressure gradients in the preselected location for determining the efficacy of drug delivery to the selected location.

The data processing system as described above can include one of (i) a display provided to receive the fourth output and display a map, (ii) a printer provided to receive the fourth output and print a map and (iii) the fourth data output being stored.

The invention further contemplates a method for monitoring a human or animal interstitial fluid pressure in space with time comprising the steps of: (a) slowly infusing a contrast agent into a human or animal; (b) monitoring a preselected volume in the human or animal for collecting data indicative of interstitial fluid pressure that varies with time as a function of at least two variables related to contrast agent concentration and fluid pressure behavior; (c) processing collected data to determine interstitial fluid pressure throughout the preselected volume with time; and providing an output indicative of one of the determined interstitial fluid pressure and concentration of contrast agent.

The method as described above can include the further step of graphically depicting the preselected volume in color to show one of interstitial fluid pressure and concentration of contrast agent; the further step of controlling delivery of a drug to the preselected volume responsive to the output of step (c); and/or the further step of administering to the human or animal a drug to lower the interstitial fluid pressure responsive to the output of step (c) indicating resistance to drug delivery. Further, infusion of the contrast agent can take place slowly, at constant or varying rates. In the method as described, the preselected volume is preferably a tumor or an organ.

Figure 2:
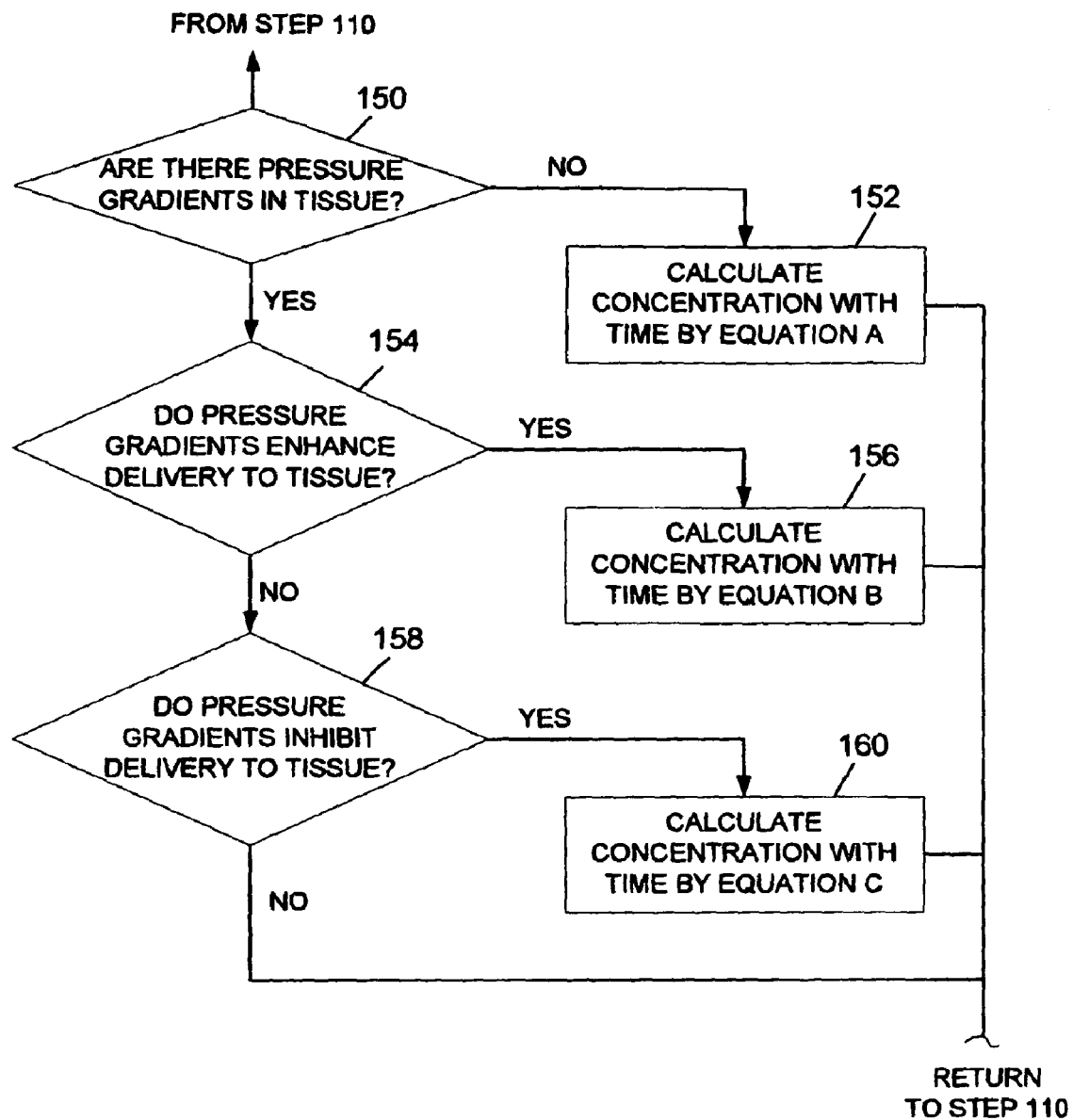
FIG. 2 shows a subroutine for the novel processing of time dependence contrast concentration.

The step of processing collected data to determine interstitial fluid pressure throughout the preselected volume with time of the method as described above can include determining pressure gradients; and can include the subroutine, as shown in FIG. 2, of processing, in Step 110, to determine concentration of contrast agent in the preselected volume on the basis of (i) if there are no pressure gradients in the preselected volume, Step 150, then determine concentration varying with time in accordance with Equation A, in Step 152, as $$C(t) = D_{inf} K_{in} \sum_{i=1}^{2} a_i \left( \frac{1 - e^{-\frac{K_{out}}{v_e} t}}{\frac{K_{out}}{v_e}} - \frac{1 - e^{-m_i t}}{m_i} \right) \Big/ \left( m_i - \frac{K_{out}}{v_e} \right) ++$$

$$v_p D_{inf} \sum_{i=1}^{2} a_i \left( \frac{1 - e^{-m_i t}}{m_i} \right)$$

where: $K_{in}$ and $K_{out}$ are the transcapillary transfer constants into and out of the tissue and are equal to each other when only concentration gradients dictate the transfer and are then defined as $k^{trans}(K_{in}=K_{out}=k^{trans})$. $D_{inf}$ is the total dose infused, $v_e$ is the fraction of free volume in the tissue (extracellular volume fraction), $v_p$ is the intravascular volume fraction and $a_i$, $m_i$ are the amplitude and clearance time constant of the contrast agent in the plasma of the blood; (ii) If there are pressure gradients that enhance delivery to the preselected volume, Step 154, determine concentration $C_t$ varying with time in accordance with Equation B, in step 156 as $$C_t(t) = D_{inf}\left(k^{trans}+k^{\Delta P}\right)\sum_{i=1}^{2} a_i\left(\frac{1-e^{-\left(\frac{k^{trans}}{v_e}\right)t}}{\frac{k^{trans}}{v_e}} - \frac{1-e^{-m_i t}}{m_i}\right) \bigg/ \left(m_i - \frac{k^{trans}}{v_e}\right) ++$$

$$v_p D_{inf} \sum_{i=1}^{2} a_i \left(\frac{1-e^{-m_i t}}{m_i}\right)$$

wherein $k^{\Delta p}$ is a pressure gradient dependent transcapillary transfer constant; and
(iii) If there are pressure gradients that inhibit delivery to the preselected volume, Step 158, determine concentration varying with time in accordance with Equation C, Step 160, as $$C_t(t) = D_{inf} k^{trans}$$

$$\sum_{i=1}^{2} a_i \left(\frac{1-e^{-\left(\frac{k^{\Delta P}+k^{trans}}{v_e}\right)t}}{\frac{k^{\Delta P}+k^{trans}}{v_e}} - \frac{1-e^{-m_i t}}{m_i}\right) \bigg/ \left(m_i - \frac{k^{\Delta P}+k^{trans}}{v_e}\right) ++$$

$$v_p D_{inf} \sum_{i=1}^{2} a_i \left(\frac{1-e^{-m_i t}}{m_i}\right)$$

wherein $k^{\Delta p}$ is in this equation a convective term dependent on the interstitial fluid pressure gradient between the center and the surrounding of a tumor (or two locations in any tissue) that washes the contrast agent outward away from the preselected volume. These refinements of the method will be explained in more detail in the following.

The invention further includes at least one stored, displayed or printed map for use in determining efficacy of a drug delivery to a preselected location in a human or animal that reflects changes in a interstitial fluid pressure in space with time after infusing a tracer/contrast agent, said at least one map based on a plurality of time intervals and being representative of, in two or three dimensions, an image of one of interstitial fluid pressure and tracer/contrast agent concentration in the preselected location wherein the discrete elements of the image have a color hue of one of a plurality of colors and a color intensity indicative of fluid pressure behavior. The map can be an image (i) displayed on a monitor; (ii) digitally encoded on a computer readable medium; or (iii) printed on a printable medium. The map can show a tumor or organ as the preselected location.

Figure 1:
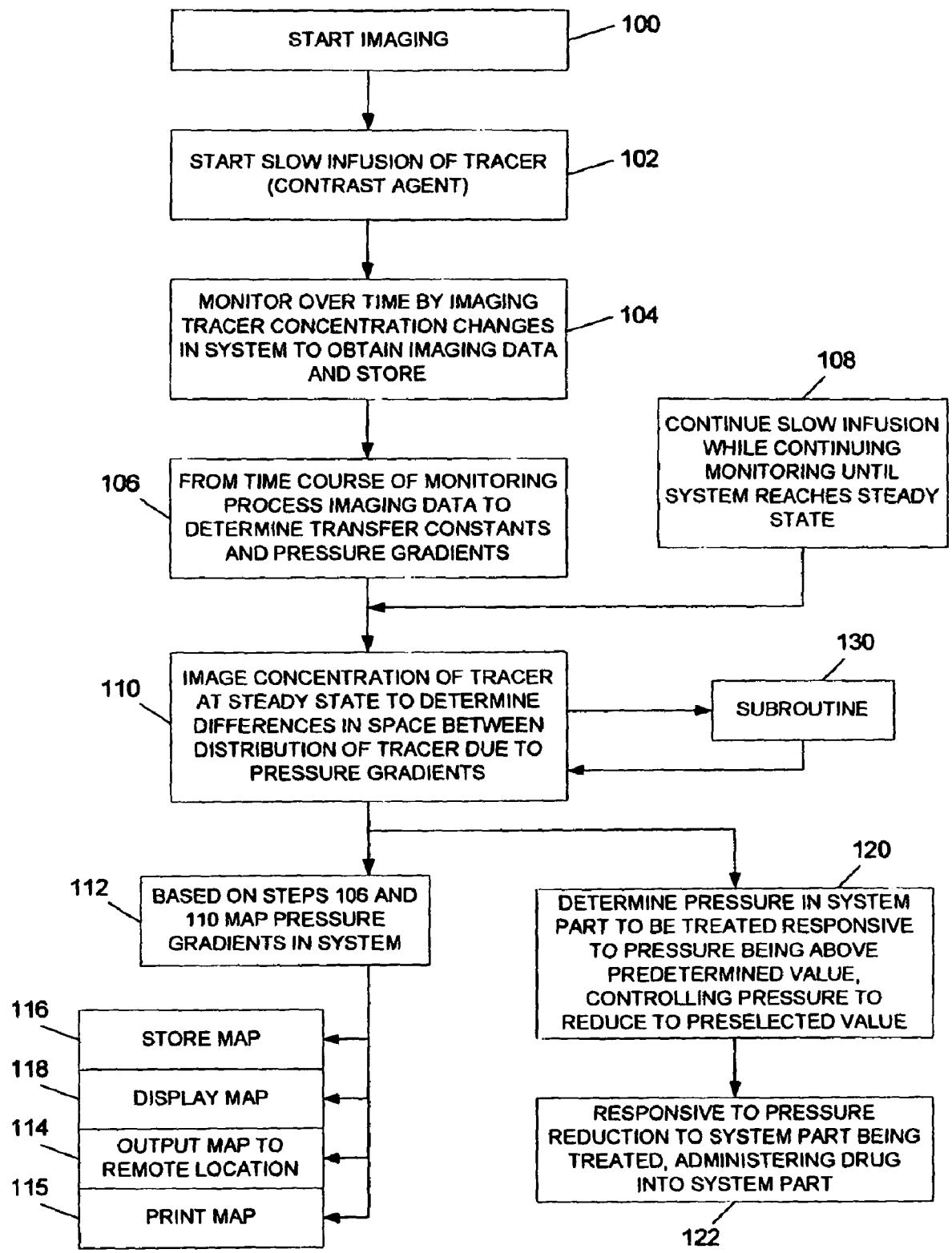
FIG. 1 shows a flow diagram of the method of the present invention.

A first embodiment of the invention is shown in FIG. 1 as a flow diagram consisting of a number of steps. In step 100 imaging is started with respect to the subject or part thereof to be monitored, such as a tumor or organ or in the body, or in specific tissues. In step 102 a tracer [contrast agent, preferably gadolinium-diethylenetriaminepentaacetic acid (Gd-DTPA)] is started, preferably by slow infusion into the subject's blood circulation. During this step, the tracer/contrast-agent is infused into the blood circulation of the subject whereby the tracer flows and enters to the whole blood circulation, as well as, is cleared out of the subject by the kidney and urine or via the liver.

In step 104 the subject is monitored over time by imaging tracer concentration changes in the subject to obtain imaging data. In step 106 from the time course monitoring of step 104, the image data obtained is processed to determine transfer constants to and from the subject and the values of pressure gradients that either help extravasation to the subject or inhibit extravasation and the results are output. Next in step 108 the infusion is continued slowly until the subject reaches steady state, namely, the amount of tracer infused is equal to the amount of tracer that is cleared out.

In step 110 the concentration of the tracer at steady state is imaged to obtain imaging data and this data is processed to determine the differences in space between the distribution of the tracer due to the presence of pressure gradients, and the results are output. Then in step 112 from the outputs and determinations of steps 106 and 110, the pressure gradients in the subject are mapped and output. The output of step 112 is alternately, sent to remote location in step 114 where it is further processed or viewed; is sent to storage in step 116; or displayed in step 118; or printed in step 115.

As further enhancements of the method of the present invention, the output from step 110 is sent to step 120 wherein it is processed to determine the pressure in the subject to be treated, and the result output. The output from step 120 is received in step 122 and processed to determine if the pressure is above a predetermined value, and the result output. The output from step 122 is received in step 124 wherein in response to the output of step 122 being a pressure above a predetermined value, the pressure is controlled in the subject by reducing the pressure to a preselected value, and an output to that effect is sent to step 126. In step 126, in response to pressure reduction in the subject to be treated, a drug is administered to the subject to be treated for a specific condition.

If the pressure in the subject or parts of the subject is high relative to the pressure in the tubes where the tracer flows (such as blood vessels) then drug delivery to the subject (or parts of the subject) will be impaired. For example, for a contrast agent or a tracer that is slowly injected into the blood vessels, the change in the concentration of the contrast agent in a tissue (or tumor) depends on specific physiological transfer constants including the pressure transfer constant into or out of the tissue. The time dependence of the tracer concentration can behave in one of the following three ways.

In the first way, if there are no pressure gradients in the tissue, the transfer force depends only on concentration gradient and then the concentration varies with time according to:

$$C(t) = D_{inf} K_{in} \sum_{i=1}^{2} a_i \left(\frac{1-e^{-\frac{K_{out}}{v_e}t}}{\frac{K_{out}}{v_e}} - \frac{1-e^{-m_i t}}{m_i}\right) \bigg/ \left(m_i - \frac{K_{out}}{v_e}\right) +$$

$$v_p D_{inf} \sum_{i=1}^{2} a_i \left(\frac{1-e^{-m_i t}}{m_i}\right)$$

Where: $K_{in}$ and $K_{out}$ are the transcapillary transfer constants into and out of the tissue and are equal to each other when only concentration gradients dictate the transfer ($K_{in}=K_{out}=k^{trans}$). $D_{inf}$ is the total dose infused, $v_e$ is the fraction of free volume in the tissue (extracellular volume fraction), $v_p$ is the intravascular volume fraction and $a_i$, $m_i$ are the amplitude and clearance time constant of the contrast agent in the plasma of the blood (usually it is assumed i=1, 2).

In areas where this equation holds, there are no pressure gradients and drugs can enter depending on the concentration gradient determined by the transfer constant K which depends on the flow and the permeability and surface area of the blood vessels, and on the fraction of blood volume, $v_p$, and the fraction of extracellular volume, $v_e$.

In the second way, if there are pressure-gradients that enhance delivery to the tissue the change in the tissue concentration, $C_t$, depends also on this pressure gradient which yields a pressure transfer constant:

$$C_t(t) = D_{inf}(k^{trans} + k^{\Delta P}) \sum_{i=1}^{2} a_i \left( \frac{1 - e^{-\left(\frac{k^{trans}}{v_e}\right)t}}{\frac{k^{trans}}{v_e}} - \frac{1 - e^{-m_i t}}{m_i} \right) / \left( m_i - \frac{k^{trans}}{v_e} \right) + + v_p D_{inf} \sum_{i=1}^{2} a_i \left( \frac{1 - e^{-m_i t}}{m_i} \right)$$

Wherein in this case the transfer constant determined by the pressure gradient, $k^{\Delta p}$, is added.

In the third way, if there are pressure-gradients in the interstitial compartment that inhibit delivery of the contrast agent (tracer) to the system with a pressure transfer constant $k^{\Delta p}$ (see arrows) the change in the concentration is:

$$C_t(t) = D_{inf} k^{trans} \sum_{i=1}^{2} a_i \left( \frac{1 - e^{-\left(\frac{k^{\Delta P}+k^{trans}}{v_e}\right)t}}{\frac{k^{\Delta P}+k^{trans}}{\uparrow v_e}} - \frac{1 - e^{-m_i t}}{m_i} \right) / \left( m_i - \frac{\downarrow k^{\Delta P}+k^{trans}}{v_e} \right) + + v_p D_{inf} \sum_{i=1}^{2} a_i \left( \frac{1 - e^{-m_i t}}{m_i} \right)$$

An outward interstitial fluid pressure gradient term (convection term) is added that washes the contrast agent outward away from the tissue.

These equations are suitable for infusion of the contrast agent at a constant rate. It is possible to design different infusion protocols, such as a bolus injection followed by slow infusion (reaching faster steady state) or infuse the contrast agent with changing rates (for example from fast to slow).

The time courses of the concentration change in the tissue can be obtained by sequential imaging of the tissue (MRI or other imaging methods). By fitting such time course to one of the above equation the contribution of the pressure term can be obtained. In the procedure used, the extracellular volume fraction is estimated from other measurements (for example from diffusion MRI studies) or by fitting the equations above to all the unknown parameters including the extracellular volume fraction, namely, $k^{trans}$ (diffusion across the capillary walls according to concentration gradients), $k^{\Delta p}$ (either due to transcapillary pressure gradients or interstitial pressure gradients), $v_e$ and $v_p$. In addition, once steady state is reached, the tissue concentration can be measured at this state and then, by incorporating $v_e$ (determined as described above) the extracellular concentration per pixel can be determined from which then the distribution of pressure can be assessed as described in a prior publication (4), which is incorporated herein in its entirety.

According to the prior publication, tumor angiogenesis facilitates blood supply and perfusion, leading to enhanced tumor growth and formation of metastasis. However, newly formed capillaries in malignant tumors usually exhibit complex and tortuous architecture and function which may elevate the interstitial fluid pressure (IFP). The increase in IFP is mainly due to increased water permeability of the tumor microvasculature and the lack of functioning, lymphatic vessels, and hence water accumulation. Additionally, intratumoral elevated IFP levels have been attributed to molecular modulations in the composition and elasticity of the tumor interstitium. The increase in IFP leads to a positive pressure gradient, which is a driving force for a convective transport back into the capillaries or to adjacent regions with low IFP. Such convective forces inhibit the transfer of drugs to the tumor interstitium and facilitate tumor cell intravasation into the vascular or lymphatic circulation, and hence promote metastasis. In regions with high IFP, the delivery of drugs may be impaired, resulting in failure of therapy. Determining IFP, and particularly the spatial distribution of the net tracer transfer to the tumor interstitium, may predict the efficiency of drug delivery and help design improved drug administration protocols. Moreover, it can help design new protocols that specifically decrease IFP or result in normalization of the vascular function. Dynamic contrast-enhanced MRI studies of fibrosarcoma mouse model have shown that a decline in IFP, induced by thalidomide, was accompanied by increased plasma volume fraction and fractional efflux rate from the interstitial space to the plasma.

The prior publication presented an alternative contrast-enhanced MRI method that revealed the distribution of the contrast material due to the net effect of extravasation, diffusion, and convection in ectopic NC1-H460 non-small-cell lung cancer tumors implanted in immunodeficient mice, which exhibit high IFP values (~28 mm Hg). For comparison, this method was applied to investigate orthotopic MCF7 human breast tumors which exhibit a significantly lower IFP (~14 mm Hg). The contrast agent was continuously administered by slow infusion into the blood circulation, raising its blood level to a steady-state concentration. The MRI recordings monitored $T_1$ relaxation rates and signal intensity before the start of the infusion and during the infusion, including at blood and tumor steady-state concentrations. Analysis of the changes in $T_1$ relaxation rates yielded steady-state tissue GdDTPA concentration (mmol/tissue volume) maps of the tumors and their surrounding. The maps reflected inhibition of transfer due to elevated tumor IFP and transfer by convection in the tumor surrounding.

MRI scans were acquired with a 4.7-T Biospec spectrometer (Bruker Biospin, Rheinstetten, Germany). Fourteen H460 tumors and nine MCF7 tumors were scanned using a protocol that included an initial two-dimensional $T_2$-weighted spin echo sequence with echo time=68 Ms; repetition time=2,500 ms; 128×128 matrix; 1-mm slice thickness; an interslice distance of 1.1; and 3×3 cm² field of view. The tumor region of interest in each slice was traced on the $T_2$-weighted images and this trace was then used for localizing the tumor in the various subsequent images obtained at the same spatial resolution. The size of the tumors was determined from the area of the region of interest and the slice thickness, taking into account the inter-slice distance. $T_1$ measurements were then done using two-dimensional sequential inversion recovery snapshot fast low-angle shot imaging with 11 inversion times ranging from 10 ms to 10 seconds; echo time=3.5 ms; repetition time=15 ms; flip angle=10 degrees; and the same matrix size and field of view as the $T_2$-weighted images. Two-dimensional $T_1$-weighted gradient echo images were also scanned using echo time/repetition time=2.73/35.8 ms; flip angle=60 degrees; and the same spatial resolution as the T2-weighted images acquiring four scans within 18 seconds. Following these measurements, slow infusion was initiated with 0.05 mol/L GdDTPA solution (gadopentate-dimeglumine, Schering, Berlin, Germany) at a rate of 0.66 mmol/h/kg wt for 2 hours, Sequential images were scanned during the slow infusion using the three-dimensional $T_1$-weighted gradient echo sequence described above. At 90 minutes after the start of infusion, $T_1$ relaxation rates were measured again using the inversion recovery snapshot fast low-angle shot sequence described above.

Separate experiments were done to monitor the GdDTPA enhancement in the carotid arteries and determine the time needed to reach steady-state in the blood during the slow infusion (n=3). In these experiments, inversion recovery fast low-angle shot sequence was applied using a fixed inversion time of 120 ms; echo time=3.5 ms; repetition time=15 ms; flip angle=10 degrees; 128×128 matrix; 1-mm slice thickness; and 3×3 cm² field of view at a temporal resolution of 6 s.

For processing and analysis, $T_1$ relaxation rates were calculated at pixel resolution applying a nonlinear least square fit of the intensity 1 per pixel at varying inversion times. The curves obtained from measurements before administration of the contrast agent and at steady-state infusion conditions exhibited a single decay time constant according to the following equation: $I=I_{inf}[1=A \exp(-TI/T_1)]$, with $I_{inf}$[maximum Intensity at a long inversion time (TI)], A (maximum value 2), and $T_1$ as the free variables in this fit with $R^2$ of the fit ranging from 0.9 to ~1. At steady-state concentration of the contrast agent in the tissues, the intracellular and extracellular $T_1$ water relaxation rates differ due to the sole presence of GdDTPA in the extracellular compartment. At a maximum concentration in the extracellular compartment of ~1 mmol/L, the upper limit for this difference is ~4 s$^{-1}$ whereas the effective intracellular-extracellular water exchange rate is more than an order of magnitude higher, 50 s$^{-1}$ (based on intracellular lifetime of ~100 ms and an intracellular to extracellular volume ratio of 4). Hence, water exchange between the intracellular and extracellular compartments is at the fast exchange limit and the $T_1$ relaxation rate at steady state is decaying uniexponentially as was indeed found in the $T_1$ measurements. Furthermore, under this fast exchange condition, tissue GdDTPA concentration ($C_{gd}$), defined as the amount of GdDTPA in millimoles per tissue volume at GdDTPA steady-state concentration, is obtained from the measured relaxation rates according to the equation $C_{gd}=(1/T_{1ss}-1/T_{10})/r_1$, where $r_1$ is the water relaxivity of GdDTPA in solution, 4.2 s$^{-1}$×(mmol/L)$^{-1}$, and $1/T_{1ss}$, and $1/T_{10}$ are the relaxation rates at steady-state concentration and before the infusion, respectively.

Maps of the actual GdDTPA concentration in the extracellular volume fraction of H460 tumors were calculated estimating an extracellular volume fraction of 0.2. The extracellular volume fraction of MCF7 tumors was determined by applying a method based on diffusion MRI. Further estimation of IFP in the H460 tumors was obtained by assuming a linear relation between IFP and the calculated GdDTPA concentration in the extracellular volume at steady state using an approximate scale of IFP between 0 mm Hg at the rim and 28 mm Hg at the center.

An attempt was made to analyze the enhancement curves during the first 30 minutes of the infusion using a kinetic model described by Tofts and Berkowitz and a nonlinear least square fit program previously developed by Bogin, Margalit, Mispelter and Degani. The output of this analysis yielded the influx and efflux transcapillary transfer rate constants.

Solid tumors of H460 non-small-cell lung cancer cells rapidly developed within a week after cell inoculation. Measurements of tumor size, obtained by analyzing the $T_2$-weighted images, showed continuous fast growth from an average size (±SD) of 110±20 mm³ (n=7) 9 days after implantation to 510±150 cm³ (n=7) a week later.

The IFP of the tumors was determined by the wick-in-needle method. Attempts were made to measure the pressure close to the center of the tumors. H460 tumors exhibited high IFP values, ranging from 18 to 45 mm Hg with a mean±SD of 28±8 mm Hg (n=7). The IFP values of MCF7 tumors were lower and more diverse, ranging from 4 to 32 mm Hg with a mean of 14±10 mm Hg (n=9). Measurement in the flank muscle opposite to the tumor site and of control mice showed IFP values ranging from 0 to 5 mm Hg.

FIG. 4A to 4D shows parametric images of $T_1$ relaxation times and calculated tissue GdDTPA concentration at steady state of an ectopic H460 tumor. FIGS. 4A and 4B show, respectively, pre-contrast $T_1$ map and steady-state $T_1$ map 90 minutes after the start of slow infusion. Tumor region of interest was delineated on the corresponding $T_2$-weighted image and duplicated on the T1 maps. FIG. 4C shows a steady-state tissue GdDTPA concentration map 90 minutes after the start of infusion. Note the heterogeneous distribution of the contrast agent in the tumor and the high tissue GdDTPA concentration outside the tumor due to outward convection. FIG. 4D shows a histologic, H&E-stained central section approximately sliced in parallel to the imaging plane.

FIG. 5A to F show parametric images of $T_1$ relaxation times and calculated GdDTPA concentration maps and profiles at steady state of an ectopic H460 tumor. FIGS. 5A and 5B show pre-contrast T, map and $T_1$ map 90 minutes after the start of slow infusion, respectively. Tumor region of interest was delineated on the corresponding $T_2$-weighted image and duplicated on the $T_1$ maps. FIG. 5C shows map of steady-state tissue GdDTPA concentration 90 minutes after the start of infusion. FIG. 5D shows map of steady-state GdDTPA concentration in the extracellular volume 90 minutes after the start of infusion. The map was derived from FIG. 5C assuming an extracellular volume fraction of –0.2 (14). FIGS. 5E and 5F show two GdDTPA concentration profiles in the extracellular volume along the lines drawn in FIG. 5D. Note the steep decrease in the concentration from the tumor rim to its center.

Figure 6A:
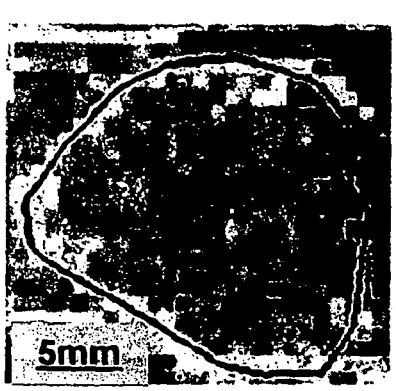
FIG. 6A to F shows parametric images of $T_1$ relaxation times and calculated GdDTPA concentration maps and profiles at steady state of an orthotopic MCF7 tumor.
Figure 6B:
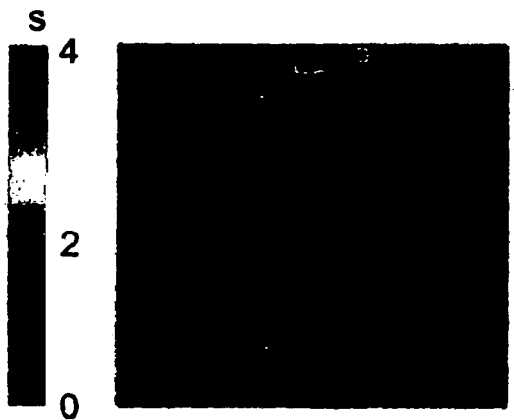
Figure 6C:
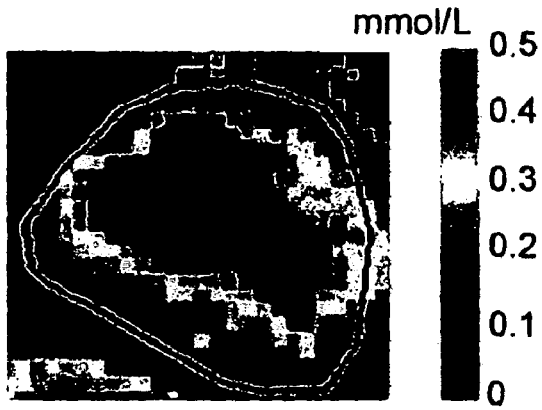
Figure 6D:
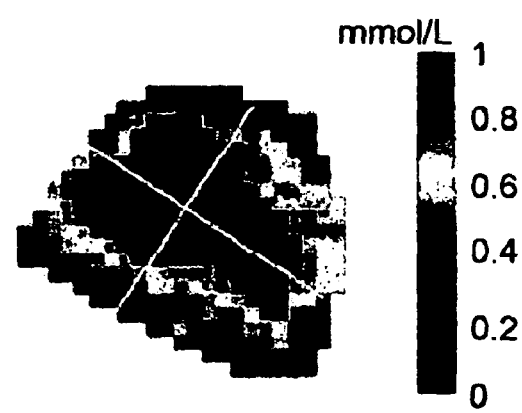
Figure 6E:
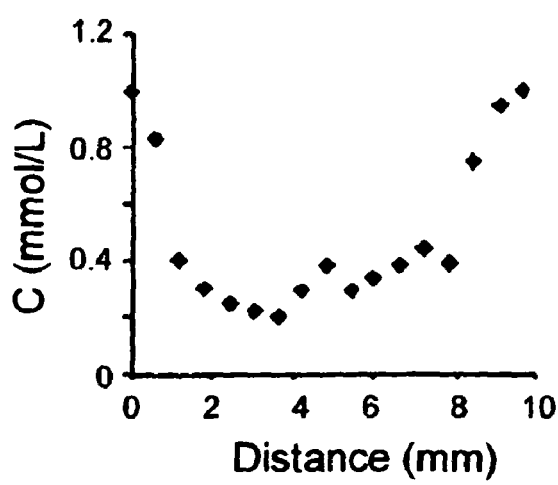
Figure 6F:
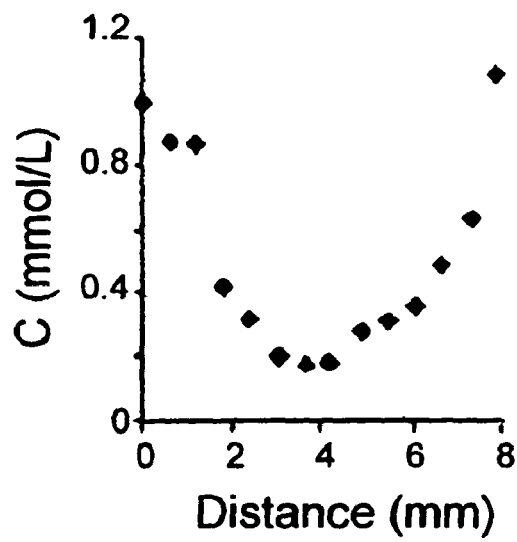

FIG. 6A to F shows parametric images of $T_1$ relaxation times and calculated GdDTPA concentration maps and profiles at steady state of an orthotopic MCF7 tumor. FIGS. 6A and 6B show pre-contrast $T_1$ map and $T_1$ map 90 minutes after the start of slow infusion, respectively. Tumor region of interest was delineated on the corresponding $T_2$-weighted image and duplicated on the $T_1$ maps. FIG. 6C shows map of steady-state tissue GdDTPA concentration 90 minutes after the start of infusion. FIG. 6D shows map of steady-state GdDTPA concentration in the extracellular volume 90 minutes after the start of infusion. The map was derived from FIG. 6C measuring a mean extracellular volume fraction of 0.4 in this tumor. FIGS. 6E and 6F show two GdDTPA concentration profiles in the extracellular volume along the lines drawn in FIG. 6D.

The IFP of this tumor was 10 mm Hg, in accord with the presence of contrast material throughout the tumor, including the center; however, there is still a descending concentration gradient from the periphery to the center.

FIG. 7 show estimated IFP maps and profiles of typical ectopic H460 tumors. The IFP maps were derived using human NC1-H460 non-small-cell lung cancer cells obtained from the American Type Culture Collection (Rockville, Md.) and were cultured as recommended by the supplier. Cells ($8 \times 10^6$), suspended in 0.5 mL PBS, were implanted s.c. into the flank of 6-week-old female CDI-NU mice. Cultivation of MCF7 cells and implantation of orthotopic MCF7 tumors were derived and implanted as previously described by Bogin and Degani. During the experiments, mice were anesthetized by inhalation of 1% isoflurane (Medeva Pharmaceuticals, Inc., Rochester, N.Y.) in an $O_2/N_2O$ (3:7) mixture applied through a nose cone.

IFP was measured in H460 tumors (n=7) 13 days after their implantation and in MCF7 tumors (n=9)~5 weeks after their implantation using the wick-in-needle apparatus. Briefly, a 23-gauge needle with a side hole located at ~3 mm from the needle tip was connected to a pressure monitor system (model 295-1 Pressure, Stryker, Kalamazoo, Mich.) especially designed for measuring tissue fluid pressures. The system was filled with saline. The needle was inserted into a central part of the tumor or into the flank muscle (n=20) for reference, and 50 µL of 0.9% sodium chloride were injected to ensure fluid communication between the tissue and the pressure monitor system. The tumor region of interest was delineated on the corresponding $T_2$-weighted image and duplicated on the maps. The IFP profiles were calculated along the lines drawn on the corresponding IFP maps. By using an approximate homogeneous interstitial volume fraction and scaling IFP according to the wick-in-needle results, an estimation of IFP distribution was obtained in the H460 tumors (FIG. 7).

Figure 8A:
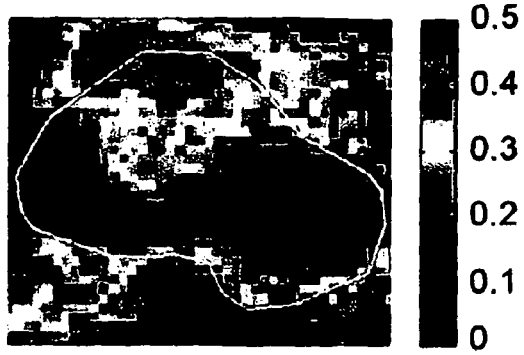
FIGS. 8A to 8F shows the results of the present invention and demonstrate the parametric images shown in FIGS. 8A to 8F that were obtained from the analysis of the slow infusion time course and from the steady state results fitting to the equations of the invention.
Figure 8B:
Figure 8C:
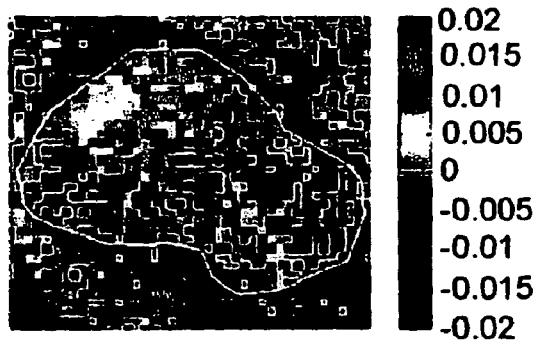
Figure 8D:
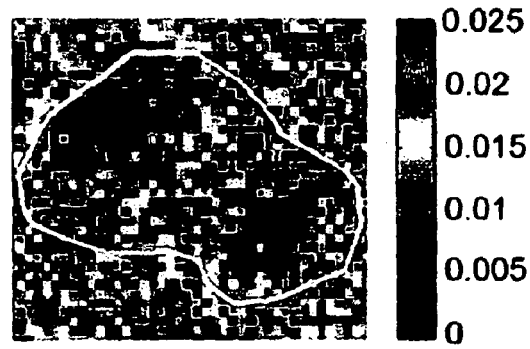
Figure 8E:
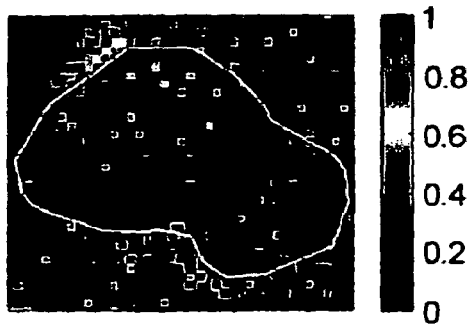
Figure 8F:
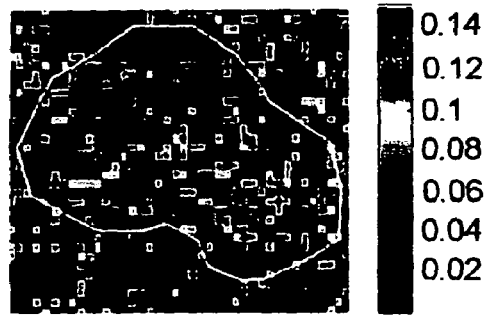

FIGS. 8A to 8F shows the results of the present invention and demonstrate the parametric images shown in FIGS. 8A to 8F that were obtained from the analysis of the slow infusion time course and from the steady state results fitting to the equations above. FIG. 8A shows the image obtained by analyzing the $T_1$ relaxation before Infusion and at steady state infusion; FIG. 8B shows the image obtained by dividing the concentration in each pixel of FIG. 8A by its $v_e$ value presented in FIG. 8E. FIG. 5C-BF show images obtained by analyzing the dynamic of contrast enhancement during slow infusion using the equations that include the pressure terms.

The Tumor steady state concentration shown in image of FIG. 8A was obtained by analyzing the $T_1$ relaxation before infusion and at steady state infusion. The extracellular steady state concentration shown in image B was obtained by dividing the concentration in each pixel of A by its $v_e$ value presented in image E. The images C to F were obtained by analyzing the dynamic contrast enhancement during slow infusion using the equations set forth above that include the pressure terms.

The present invention can be realized in hardware, software, or a combination of hardware and software. A system according to a preferred embodiment of the present invention can be realized in a centralized fashion in one computer system, or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

An embodiment of the present invention can also be embedded in a computer program product, which comprises all the features enabling the implementation of the methods described herein, and which—when loaded in a computer system—is able to carry out these methods. Thus a computer readable medium containing instructions for carrying out the method of the present invention is novel and useful. Computer program means or computer program in the present context mean any expression, in any language, code or notation, of a set of instructions intended to cause a system having an information processing capability to perform a particular function either directly or after either or both of the following a) conversion to another language, code or, notation; and b) reproduction in a different material form.

A computer system may include, inter alia, one or more computers and at least a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network that allow a computer system to read such computer readable information.

Figure 3:
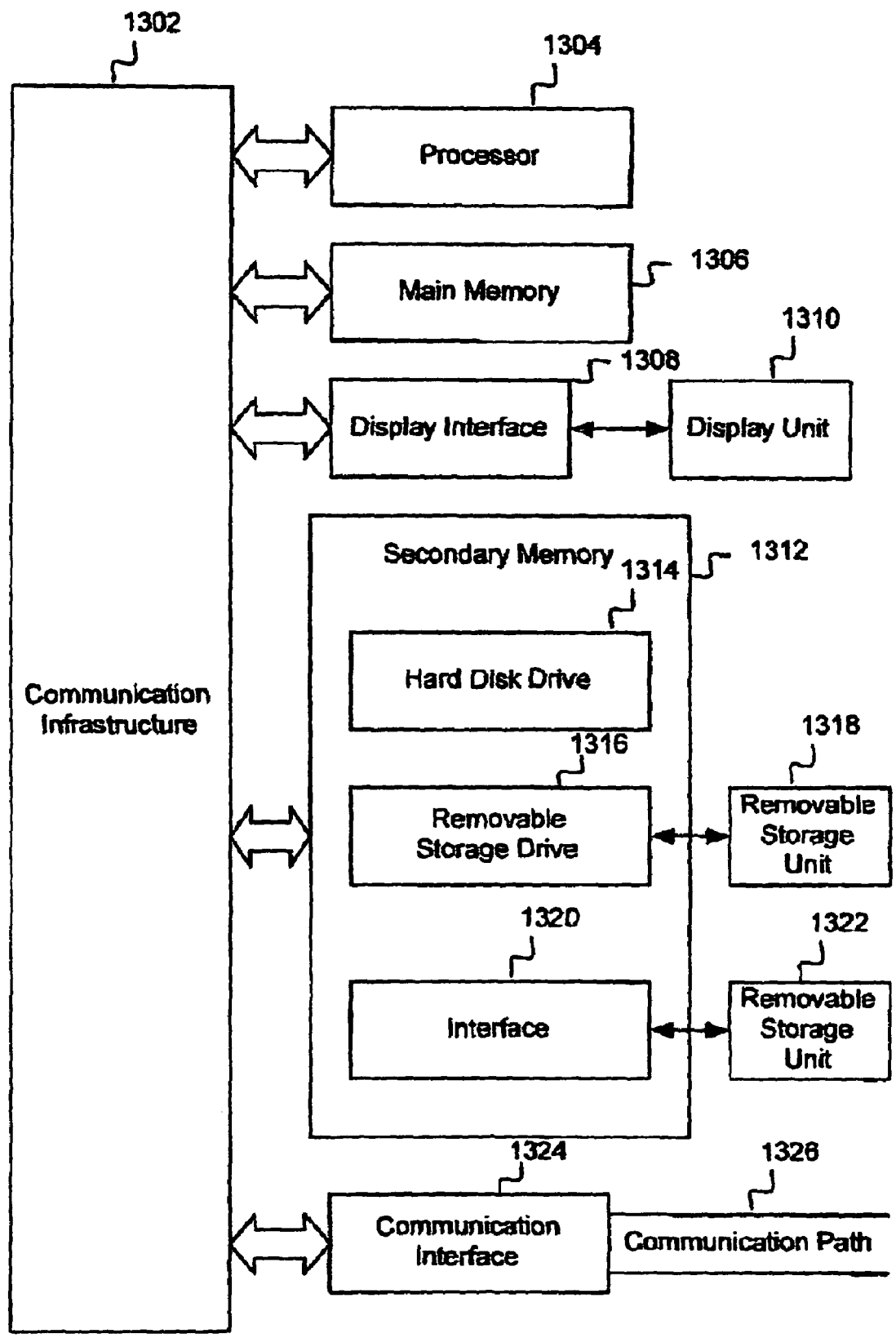
FIG. 3 shows a computer system for use with the present invention.

FIG. 3 is a block diagram of a computer system useful for implementing an embodiment of the present invention. The computer system includes one or more processors, such as processor 1304. The processor 1304 is connected to a communication infrastructure 1302 (e.g., a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

The computer system can include a display interface 1308 that forwards graphics, text, and other data from the communication infrastructure 1302 (or from a frame buffer not shown) for display on the display unit 1310. The computer system also includes a main memory 1306, preferably random access memory (RAM), and may also include a secondary memory 1312. The secondary memory 1312 may include, for example, a hard disk drive 1314 and/or a removable storage drive 1316, representing a floppy disk drive, a magnetic tape drive, an optical disk drive, and more. Removable storage drive 1316 reads from and/or writes to a removable storage unit 1318 in a manner well known to those having ordinary skill in the art. Removable storage unit 1318 represents a floppy disk, magnetic tape, optical disk, and more which is read by and written to by removable storage drive 1316. As will be appreciated, the removable storage unit 1318 includes a computer usable storage medium having stored therein computer software and/or data.

In alternative embodiments, the secondary memory 1312 may include other similar means for allowing computer programs or other instructions to be loaded into the computer system. Such means may include, for example, a removable storage unit 1322 and an Interface 1320. Examples of such may include a program cartridge and cartridge interface (such as that found in video game devices), a removable memory chip (such as an EPROM, or PROM) and associated socket, and other removable storage units 1322 and interfaces 1320 which allow software and data to be transferred from the removable storage unit 1322 to the computer system.

The computer system may also include a communications interface 1324. Communications interface 1324 allows software and data to be transferred between the computer system and external devices. Examples of communications interface 1324 may include a modem, a network interface (such as an Ethernet card), a communications port, a PCMCIA slot and card, and more Software and data transferred via communications interface 1324 are in the form of signals which may be, for example, electronic, electromagnetic, optical, or other signals capable of being received by communications interface 1324. These signals are provided to communications interface 1324 via a communications path (i.e., channel) 1326. This channel 1326 carries signals and may be implemented using wire or cable, fiber optics, a phone line, a cellular phone link, an RF link, and/or other communications channels. In this document, the terms "computer program medium," "computer usable medium," and "computer readable medium" are used to generally refer to media such as main memory 1306 and secondary memory 1312, removable storage drive 1316, a hard disk installed in hard disk drive 1314, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information.

Computer programs (also called computer control logic) are stored in main memory 1306 and/or secondary memory 1312. Computer programs may also be received via communications interface 1324. Such computer programs, when executed, enable the computer system to perform the features of the present invention as discussed herein. In particular, the computer programs, when executed, enable the processor 1304 to perform the features of the computer system. Accordingly, such computer programs represent controllers of the computer system.

As has been noted, solid tumors often develop high interstitial fluid pressure as a result of increased water leakage and impaired lymphatic drainage. This high pressure forms a barrier to drug delivery and hence, resistance to therapy. The novel, non-invasive method of the present invention based on MRI which maps throughout the entire tumor the vascular parameters serves to determine the efficiency of drug delivery. The inventive method has been applied to non-invasively monitoring the effects of collagenase, which reduces interstitial hypertension, and was tested in H460 ectopic human non-small-cell lung cancer xenografts in immunodeficient mice. Sequential images were recorded during slow infusion of a Gd-based contrast agent and were analyzed using an extended mathematical model of tumor perfusion. The final output provided vascular parameters such as concentration dependent and pressure dependent transfer constants, as well as intravascular and extracellular volume fractions. The tumors exhibited positive pressure dependent transfer constants at the boundaries and negative pressure dependent transfer constants in internal region. These negative transfer constants reflected increased interstitial fluid pressure as was confirmed by using the wick in needle method. After treatment with collagenase there was a significant increase in the pressure dependent transfer constant, from negative to positive values, in the tumors' central regions. The results demonstrated that the inventive MRI method can map at high spatial resolution the barriers to successful delivery of drugs and provide a quantitative measure for testing new drugs that eliminate these barriers.

Resistance of solid tumors to anti-neoplastic agents is a complex phenomenon resulting from processes occurring both inside tumor cells and within their surrounding microenvironment: the microvascular network, stromal components and extracellular matrix. Intracellular mechanisms of resistance involve the activation of multidrug resistance genes and drug export pumps, as well as alterations in metabolic pathways which may prevent the activity of drugs in the tumor (5, 6). Resistance to drug delivery, which develops in the tumor microenvironment, is mainly caused by impaired function of the microvasculature and lymphatic systems that leads to increased interstitial fluid pressure (IFP) (7). In healthy tissues with normal microvascular perfusion and lymphatic drainage, the IFP is close to zero mm Hg resulting in a positive transcapillary pressure gradient which favors extravasation of the drugs. In tumors, however, the increase in the capillary permeability and impaired lymphatic drainage augment IFP to values ranging from 7 mm Hg to as high as 40 mm Hg, thereby reducing and at times even eliminating the transcapillary pressure gradient and inducing outward interstitial convection which forces compounds out of the tumor.

In addition to the consequences of the changes in the properties of the blood and lymphatic vessels in tumors, the stroma of solid tumors also actively participates in increasing IFP. It has been proposed that interstitial fluid pressure is normally regulated through interactions between the extracellular matrix (ECM) and stromal cells. The extravasation of plasma macromolecules such as fibrinogen through the permeable vasculature of the progressing tumor and a high deposition of collagen lead to the formation of a very dense network of matrix molecules in the tumor. Fibroblasts can easily proliferate in this specific microenvironment and eventually gain contractile function through the acquisition of smooth muscle cell properties. The binding of "activated" fibroblasts to interstitial fibers via a variety of integrins leads to increased pressure within the tumor ECM (8).

Several studies performed on animal models showed that the abnormal distribution of the pressure gradients in high IFP tumors attenuate drug delivery and may result in the failure of chemotherapy ((9),(10) and the references cited there in). High IFP has been also demonstrated in human tumors such as breast carcinoma (11, 12), metastatic melanoma (11, 13, 14), head and neck carcinoma (15), colorectal carcinoma (11), and cervical carcinoma (16). The studies of cervical cancer demonstrated that the survival rate of patients with tumors exhibiting low IFP (IFP<19 mm Hg) was significantly higher than that of patients bearing tumors with high IFP (17). Furthermore, IFP levels in cervical cancer also showed a negative correlation with transcapillary transfer constants derived from dynamic contrast enhanced MRI studies, suggesting impaired extravasation of blood borne molecules with increased IFP.

Different approaches for improving drug delivery to high IFP tumors were proposed and tested (18-25). Recent studies also showed that treatment with agents that modulate the tumors' stromal tissue components can lead to decreased IFP. For example, Eikenes et al measured the effect of collagenase, an enzyme that by degrading collagen modulates the assembly of fibroblasts and collagen fibers, on the IFP in human osteosarcoma xenografts. They found that collagenase (0.1%) reduced IFP within hours inducing a 2-fold increase in the tumor uptake and distribution of a monoclonal antibody (26).

A major drawback that inhibits detection of resistance stemming from impaired delivery, as well as the development of new agent for modulating interstitial pressure, is the lack of a non invasive imaging technique for mapping IFP. The current methods for determining IFP, such as, the Perforated capsule (Micropore chamber) method, the wick-in-needle technique, or the micropipettes and servo null device are invasive, limited to few locations in a tissue and consequently not clinically practical.

The method and apparatus of the present invention provide a novel, non invasive MRI method for mapping the parameters that determine tumor perfusion, particularly, transfer due to pressure gradients resulting from the distribution of IFP in tumors. This comprehensive method, based on dynamic images obtained during infusion of contrast agents, was complemented by a steady state infusion method developed previously as noted above (4). The performance of the method has been demonstrated in non small cell lung cancer xenografts that exhibit high interstitial fluid pressure. The resulting perfusion parameters provided a means by which to separately map concentration- and pressure-dependent transfer constants, in addition to intravascular and extracellular volume fractions. The application of this method to monitor temporal changes in IFP was demonstrated by modulating the pressure with collagenase. This treatment clearly showed that altering the extracellular matrix constituents can significantly reduce IFP and improve tumor perfusion.

The functional microvascular parameters of H460 human non-small-cell lung cancer tumors implanted ectopically into the flanks of female CDI nude immunodeficient mice were investigated by the novel MRI method based on slow infusion of a contrast agent. The tumors were scanned two weeks after implantation, by which point they had reached a median size of 18 mm$^3$ (n=11) as determined by standard T2 weighted images (ref). The interstitial fluid pressure of each tumor was measured using the wick in needle method (27), inserting the needle into an inner part of the tumor. All tumors exhibited a relatively high IFP with an average of 31±7 mm Hg, (n=11).

Histologically, the tumors were composed of viable, densely-packed cancer cells with small scattered regions of necrosis (FIG. 10A). The high cellular density and low fraction of extracellular spaces appeared to be similar throughout the whole tumor. The distribution of the blood capillaries in the tumors was revealed by CD31 immunostaining. Overall the staining revealed the presence of capillaries throughout the whole tumor (FIG. 10B). Statistical analysis did not show a significant difference between the density of capillaries in the rim and the center of the tumors and yielded a mean capillary volume fraction of 6±3%.

Magnetic resonance imaging of H460 human non-small-cell lung cancer tumors implanted ectopically into the flanks of female CD1 nude immunodeficient mice was applied before and during intravascular infusion of the common gadolinium-based contrast agent, gadolinium-diethylenetriaminepentaacetic acid (GdDTPA; 0.011 mmol/min/kg body wt), and after it reached steady state.

Figure 11A:
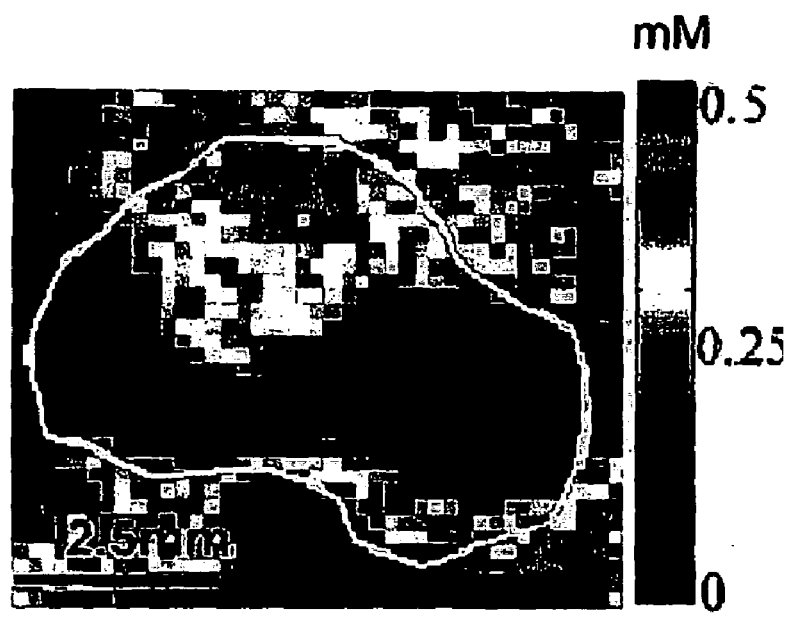
FIG. 11A showing a tumor in which GdDTPA at steady state reached all areas at varying concentrations.
Figure 11B:
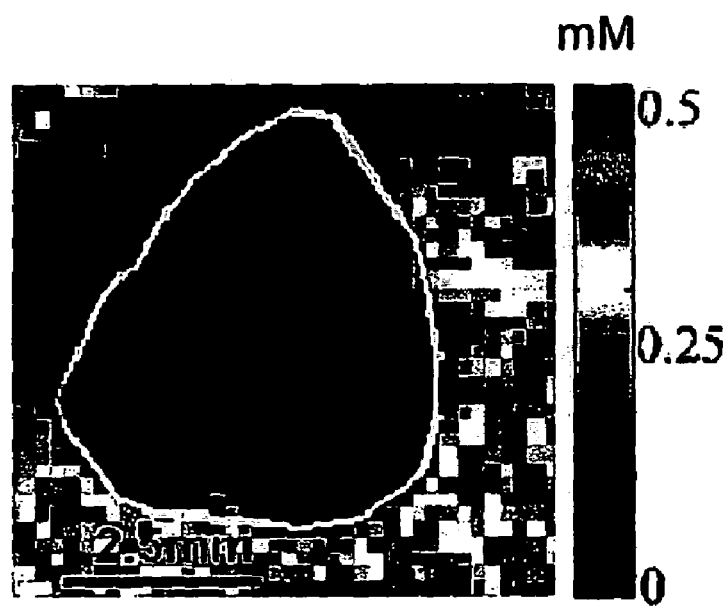
FIG. 11B showing a tumor in which GdDTPA at steady state did not reach part of the tumor interior; maps were calculated from $T_1$ relaxation rates measured before and during infusion of GdDTPA, when it reached steady state; the boundary of each tumor, marked in white, was initially outlined on the $T_2$ weighted image and transferred to the corresponding maps of the vascular parameters.

The images recorded during the steady state infusion of the contrast agent revealed that it was distributed heterogeneously within the tumor tissue; two typical examples are shown in FIG. 11. In some tumors, the contrast agent entered most of the areas within the tumor boundary, albeit in varying concentrations (FIG. 11A). In other tumors, little or no contrast agent was found in much of the tumor interiors (FIG. 11B). Low or null concentrations in the interior regions suggested the presence of high interstitial fluid pressure in accord with the measurements by the "wick-in-needle" method.

The temporal intensity changes in the images were analyzed using an extended physiological model that included transfer due to pressure gradients induced extravasation and convection (see supplemented material) and home designed software. The analysis yielded parametric maps of a concentration-derived transcapillary transfer constant, ($k^{trans}$), a pressure-derived transcapillary transfer constant which reflected a positive pressure gradient ($+k^{\Delta p}$) leading to extravasation, or a negative pressure gradient ($-k^{\Delta p}$) due to high interstitial fluid pressure, leading to outward convection; an intravascular volume fraction ($v_p$); and an extracellular extravascular volume fraction ($v_e$), as shown in FIG. 12 for a representative tumor. The goodness of the fitting was assessed by determining the proportion of variability ($R^2$) (see methods). The distributions of the parameters $k^{trans}$, $+/-k^{\Delta p}$, $v_p$, and $v_e$ were not always symmetric around the mean (FIG. 12); hence, the median values were used for each tumor to summarize the statistics of these parameters for all tumors (Table 1 appended).

The pressure-dependent transfer constant was predominantly positive at the rims of all the tumors, indicative of extravasation, and predominantly negative in the internal regions, suggesting an increase in interstitial fluid pressure leading to outward convection (FIG. 12). In some of the tumors (n=5), the enhancement in the interior part of the tumors was too small to be detected (FIG. 11B), suggesting very high interstitial fluid pressure in this region leading to strong outward convection and net non detectable or null concentrations of the contrast agent. Statistical analysis of the four vascular parameters in all tumors (disregarding pixels with null enhancement) (Table 1 appended) showed that the pressure-dependent transcapillary transfer constants exhibited the largest variations between individual tumors, as compared to the other parameters. The average extracellular volume fraction of 0.2±0.03 and the relatively low standard deviation is in accord with the high density of the cells and the even distribution of cells throughout the tumor volume as was revealed by histopathology (FIG. 10). The intravascular volume fraction of approximately 3.7±1.2% is also within the range found for this parameter by immunostaining of the capillaries (6±3%).

Taken together, these results demonstrate the significant effect of pressure gradients on the distribution of soluble substances in tumors and the importance of measuring these gradients in vivo. Interestingly, in some tumors, the impact of interstitial hypertension may reduce or even completely eliminate delivery of drugs to the tumor interior although small nutrients and oxygen may still reach these regions and maintain their viability.

The presence of high interstitial fluid pressure in the tumor interior, and the marked reduction in this pressure close to the tumor boundaries, was further substantiated by correlating the pressure gradients dependent transfer rates derived from the dynamic analysis, with the interstitial concentrations of the contrast agent at steady state (FIG. 13). The rim of the tumors with high positive pressure gradients showed high interstitial concentrations of the contrast agent, whereas interior parts of the tumors with low or negative pressure gradients displayed low interstitial concentrations of the contrast agent. A congruence between the dynamic analysis and the steady-state measurements was statistically significant (p<0.00001) as demonstrated by the pixel-by-pixel Pearson correlation curves illustrated in FIG. 13, c and f. In contrast, no correlation was found between the steady state concentration and all other parameters determined by the analysis suggesting that indeed the steady state maps were determined by pressure gradients.

Finally, the capability of the method was also demonstrated to detect a change in IFP induced by treatment with collagenase. Collagenase catalyzes the degradation of collagen fibers. Changing the collagen microfibrillar network in tumors modulates the extracellular matrix and causes a decrease in IFP (10, 26). H460 tumors were monitored during infusion, in the dynamic period and at steady state 24 h before and ~5 h after collagenase administration (0.4 mg/kg body w). FIG. 14 shows tissue concentration maps at steady state infusion and profiles of the concentration change across the tumor before and after collagenase treatment. Before treatment the contrast agent barely entered the tumor as a result of high IFP and induced outward convection, however, after treatment the outward convection vanished and the transfer of the contrast agent in the interior regions of the tumor markedly increased indicating a reduction of IFP. Similarly, maps of transcapillary transfer due to pressure gradients, $k^{\Delta P}$, and the profiles of this parameter across the tumor indicated a change, particularly in the tumor's central region, from a negative $k^{\Delta P}$ before collagenase to a null or positive $k^{\Delta P}$ after collagenase (FIG. 6). This collagenase induced change was confirmed statistically: $k^{\Delta P}$ in the internal parts of the tumors significantly increased from $(-2.6 \pm 3.7)*10^{-3}$ to $(8.6 \pm 8.9)*10^{-3}$ (n=14, paired t-test, p=0.016) following collagenase treatment, whereas all other vascular parameters derived from the analysis did not change significantly (Table 2 appended).

The inventive non-invasive high spatial resolution imaging method developed and tested can assess the capacity of a tumor capillary network to deliver a soluble substance into the tissue. This novel method is based on the application of contrast-enhanced magnetic resonance imaging, employing a clinically approved gadolinium-based contrast agent that is slowly infused into the blood circulation. An extended physiological model was used to analyze the time courses by which the contrast agent entered the tumors enabling separation of the transfer constants due to concentration and pressure gradients, and mapping each of them throughout the entire tumor. The efficacy of the method to monitor temporal changes in the distribution of the barriers to drug delivery has been demonstrated in non-small-cell lung cancer xenografts treated with collagenase, which reduces the interstitial fluid pressure.

There is increasing interest in developing ways to improve drug delivery, particularly in cancer patients. A main obstacle to successful drug delivery in solid tumors is increased interstitial fluid pressure (10),(28). A marked increase in tumor IFP reduces the transcapillary pressure gradient that leads to extravasation, and creates a driving force toward outward convective transport through the interstitial spaces to adjacent regions in the tumor periphery with low IFP. This mechanism inhibits the net transfer of drugs to the tumor interstitium and presents a mode of physical resistance to chemotherapy.

In the past, several imaging methods such as computed tomography (CT), positron emission tomography (PET), single photon emission computed tomography (SPECT), and MRI were employed for mapping the distribution of a specific drug or contrast agent within tumors (29-32); however, no attempts were made to determine the various mechanisms of transfer and separate the effects of concentration gradients and pressure gradients. Model based analyses of high spatial resolution contrast enhanced MRI data following a bolus injection of the contrast agent yielded parametric images or average values of parameters such as the influx transcapillary transfer constants and the extracellular volume fraction (33, 34). In these models the contribution of pressure gradients were not taken into account and only concentration dependent diffusion across the capillary walls were considered. In a recent study of orthotropic breast cancer tumors in nude mice the analysis included a disparity between the inward and outward transcapillary transfer constants to account for the high interstitial fluid pressure. In a study of a murine sarcoma tumor, Zhao et al have used dynamic contrast enhanced-MRI data and a physiological model that accounted for extravasation induced by pressure gradients across the capillary walls and in the interstitial space to simulate the IFP distribution and outward interstitial velocity.

As previously demonstrated that measuring the concentration of the contrast agent within the tumor tissue at steady state and imaging its heterogeneous distribution, could provide a means for mapping the interstitial fluid pressure throughout the entire tumor (4). It is now demonstrated that analyzing the contrast enhanced changes during the infusion of a contrast agent using equations that include the influence of pressure gradients, makes it possible to map the pressure dependent transfer constants throughout the tumor non-invasively. This method reduces both the length of the measurement and the amount of perfused contrast agent as compared to the steady state method. Overall, the parameters extracted by this method, enable to characterize the functional properties of the capillary network and its ability to deliver substances throughout the tumor tissue.

It should be pointed out that important general dilemmas arise when dynamic contrast enhanced time courses are fitted to complex non linear equations with several free parameters: 1. The values of the resultant physiological parameters may represent accidental results due to convergence in a local minima and are not the factually correct tissue parameters, 2. There is no "ground truth" that can confirm correctness of the fitted parameters. These dilemmas are not resolved, but the novel method is able to show a semi-quantitative agreement between the MRI derived parameters ($v_e$, $v_p$) and the cellular and vascular density obtained by histopathology and immunostaining. In addition, the IFP measurements using the wick in needle method confirmed the presence of high IFP inside the tumors.

Another validation of the parameters obtained from the dynamic MRI curves was obtained by demonstrating a high correlation between the distribution of the contrast agent at steady state (obtained by an independent MRI method) and the distribution of the pressure-dependent transfer constant $k^{\Delta P}$. Thus, by using two independent MRI measurements of contrast agent distribution, one during the dynamic phase and the other at steady state, the inventive method was able to map the pressure gradients and the steady-state concentrations of the contrast agent within the tumor tissue, both of which revealed the detailed distribution of a physical barrier to delivery in the interior regions of the tumors. This distribution indicated high interstitial fluid pressure in interior parts of the tumors which dropped precipitously at the tumor margins, as was previously predicted theoretically (35)(1) and shown experimentally (26, 36, 37).

The noninvasive nature of the method developed also enabled monitoring in real time the efficiency to affect the elasticity of the extracellular matrix in reducing IFP using collagenase (10, 26). This demonstrated a significant change in the pressure gradient dependent transfer constant in the internal parts of the tumors by collagenase treatment, from a negative value indicative of high IFP to a positive value reflecting a decrease in IFP (Table 2 appended). The steady state tissue GdDTPA concentration in the internal parts also significantly increased after collagenase treatment. Thus, the method developed provides a novel means to test the efficiency of new drugs that reduce IFP and overcome this physical resistance to chemotherapy.

The first attempts to reduce IFP involved administration of drugs that influence blood pressure and flow in order to increase the pressure gradient from the capillaries outwards and improve extravasation to the tumor tissues. However, the results were not consistent and the agents were not specific to the tumor tissue and demonstrated cardiovascular side effects (18-21).

Another approach to reduce IFP was based on degradation of the ECM (38); (26); (39). Intra-tumoral injection of collagenase or hyaluronidase was shown to reduce IFP and to increase the uptake of antibodies. It is also showed herein that collagenase reduces IFP and increases the uptake of a contrast agent within hours after its administration. However, as the use of such enzymes is not selective and may also facilitate tumor metastasis and hence more selective drugs targeted to the tumors ECM needs to be developed.

More recently the use of anti-angiogenic agents, such as monoclonal antibodies against VEGF or against VEGF receptors, were introduced in conjunction with chemotherapy. It was proposed that administration of these drugs normalizes the functional properties of the capillary network in tumors thereby reducing IFP and increasing chemotherapy delivery (22-25). Using our method it is now possible to provide a clear evidence to this hypothesis.

The use of a common, clinically approved contrast agent and the non invasive nature of MRI make it possible to extend the method to humans. Such an extension requires adjusting the infusion protocol to its faster pharmacokinetics in humans and optimizing the dose to the minimum level necessary to obtain sufficient enhancement close to steady state.

In summary, the inventive method has demonstrated the feasibility of using magnetic resonance imaging and a common gadolidium-based contrast agent infused at a slow rate, to provide information how a complex vascular network would deliver soluble substances throughout the tumor and surrounding tissues. Translation of this novel, non-invasive imaging method to humans could facilitate clinical evaluation of therapeutic modalities and prediction of patient response, particularly to novel anti-angiogenic drugs that are now being developed. Further studies in the clinic are required to ultimately reach this goal.

The inventive method and apparatus were tested on cells and tumors in animals.

Human NCI-H460 non small cell lung cancer (NSCLC) cells were cultivated and implanted into the flanks of female CD1-NU immunodeficient mice, as previously described (4). During the MRI experiments, mice were anaesthetized by inhalation of 1% isofluorane (Medeva Pharmaceuticals, Inc., Rochester, N.Y., USA) in an $O_2/N_2O$ (3:7) mixture applied through a nose cone (4). Collagenase (Sigma-Aldrich, St Louis, Mo., USA) treatment was applied by i.v. injection of 0.4 mg/kg body w of this enzyme (1 mg=161 collagen digestion units).

IFP of the tumors was measured immediately after the MRI experiment (see following) using the wick-in-needle method (4). Tumors were then removed for histopathological analysis using hematoxylin and eosin staining, as well as CD31 immunostaining, as previously described (4). All animal protocols were approved.

MRI scanning was performed on a 4.7-T Biospec spectrometer (Bruker Biospin, Rheinstetten, Germany) employing the same spatial resolution of $0.2 \times 0.2 \times 1$ mm$^3$ in all protocols. Delineation of the boundary of the tumors and determination of their volume was achieved by analyzing images recorded with a 2-dimensional fast spin echo sequence using TE/TR=49|3000 ms as previously described (40).

Tissue contrast agent concentration at steady state infusion was determined from measurements of $T_1$ relaxation rates before, and at 90 min after the start of the intravenous infusion of the contrast agent as previously described (4). For the dynamic measurements 3-dimensional $T_1$. weighted gradient echo images were recorded using TErTR=2.1/18.3 ms and flip angle=45°, 47 s temporal resolution. After recording 5 pre-contrast images, slow infusion of GdDTPA (gadopentate-dimeglumine, Schering, Berlin, Germany) was initiated at a rate of 0.011 mmol/min/kg body wt. for a total time of 120 min.

Analysis of the dynamic data collected during the slow infusion was performed at pixel resolution, on the basis of a model proposed by Jain et al (1, 35, 41-43). This model takes into account the transfer of solutes through the capillary walls and within the interstitial spaces by both diffusion in the direction of the concentration gradients and convection in the direction of the pressure gradients. Relying on few assumptions, which are described herein two differential equations were solved. The first equation applies to regions with low IFP were positive pressure gradients favors net transfer of contrast agent from the capillaries into the tissue (see equation 1) and the second one applies to intra tumoral regions with high IFP where a pressure gradients in the interstitium favors outward convection of the contrast agent and reduces the net delivery to these regions (see equation 2).

$$C_t(t) = D_{inf}(k^{trans} + k^{\Delta P}) \qquad (2)$$

$$\sum_{i=1}^{2} a_i \left( \frac{1 - e^{-\left(\frac{k^{trans}}{v_e}\right)t}}{\frac{k^{trans}}{v_e}} - \frac{1 - e^{-m_i t}}{m_i} \right) \Bigg/ \left( m_i - \frac{k^{trans}}{v_e} \right) ++$$

$$v_p D_{inf} \sum_{i=1}^{2} a_i \left( \frac{1 - e^{-m_i t}}{m_i} \right)$$

$$C_t(t) = D_{inf} k^{trans} \sum_{i=1}^{2} a_i \left( \frac{1 - e^{-\left(\frac{k^{\Delta P}+k^{trans}}{v_e}\right)t}}{\frac{k^{\Delta P}+k^{trans}}{v_e}} - \frac{1 - e^{-m_i t}}{m_i} \right) \Bigg/$$

$$\left( m_i - \frac{k^{\Delta P}+k^{trans}}{v_e} \right) ++ v_p D_{inf} \sum_{i=1}^{2} a_i \left( \frac{1 - e^{-m_i t}}{m_i} \right)$$

Where Ct is the contrast agent concentration in the entire tissue, $D_{inf}$ is the contrast agent-infusion rate, $k^{trans}$ the transcapillary transfer constant, $k^{\Delta P}$ the pressure gradients derived transfer rate which also depends on the shape, morphology, and the hydraulic conductivity of the tissue (1). $v_e$ represents the extracellular extravascular (EES) volume fraction, and $v_p$ the intravascular volume fraction. The parameters $a_i$, and $m_i$ (i=1,2) represent the average plasma pharmacokinetic amplitude and time constant parameters, respectivelyt calculated to be $a_1$=2.94 kg/l, $a_2$=4.85 kg/l, $m_1$=0.73 min$^{-1}$, and $m_2$=0.075 min$^{-1}$ as previously reported (44).

A nonlinear "best fit" algorithm (40) was applied to fit the time courses to Equations 1 and 2, calculating the proportion of variability, $R^2$, per pixel for each fitting. A combined $R^2$ map, produced by choosing in each pixel the higher $R^2$ among the two fittings and using a general threshold of $R^2 \geq 0.7$ served to obtain the final maps of the vascular parameters.

Tissue GdDTPA concentration ($C_{Gd}$) at steady state was calculated at pixel resolution from the $T_1$ measurements, as previously described (4).

Maps of GdDTPA concentrations in the interstitial space were calculated by dividing the value of the tissue GdDTPA concentration by the corresponding Ve value obtained from the dynamic analysis, for each pixel.

The means of median±standard deviation (SD) of each vascular parameter for all 11 tumors were calculated using the median value of each parameter in all the pixels of each tumor. The congruence between the interstitial GdDTPA concentration and the pressure gradient dependent transfer constants was evaluated using a Pearson correlation, which yielded a correlation coefficient r and its statistical significance.

Paired t-test was applied to evaluate the effect of collagenase treatment on the vascular parameters using p<0.05 to indicate significance.

TABLE 1

Statistical analysis of the vascular parameters in H460 tumors

| Parameter | Mean of median ± (SD) (n = 11) |
| --- | --- |
| $k^{trans} \times 10^{-3}$, min$^{-1}$ | 7.1 ± 2.8 |
| $+k^{\Delta p} \times 10^{-3}$, min$^{-1}$ | 4.9 ± 5.0 |
| $-k^{\Delta p} \times 10^{-3}$, min$^{-1}$ | 1.5 ± 1.0 |
| $v_e$ | 0.20 ± 0.03 |
| $v_p$ | 0.037 ± 0.012 |

Note from the figures that the center of the tumors exhibited negative $k^{\Delta p}$ suggesting high IFP and convection outward, whereas the peripheral regions exhibited positive $k^{\Delta p}$ suggesting extravasation from the capillaries into low IFP regions.

TABLE 2

Statistical analysis of the vascular parameters inside H460 tumors (excluding the rim), 24 h before, and 5 h after collagenase administration. (n = 12)

| parameter | Before collagenase | After collagenase | p value |
| --- | --- | --- | --- |
| $K^{\Delta p}*10^{-3}$ | -2.6 ± 3.7 | 8.6 ± 8.9 | 0.016 |
| $K^{trans}*10^{-3}$ | 3.9 ± 3.0 | 3.7 ± 3.4 | 0.76 |
| $v_e$ | 0.23 ± 0.07 | 0.24 ± 0.06 | 0.64 |
| $v_p$ | 0.063 ± 0.019 | 0.053 ± 0.027 | 0.19 |

Note that only the pressure dependent transfer constant changed and increased significantly after the administration of collagenase suggesting decreased IFP in the center.

Although the invention has been shown and described in terms of preferred embodiments, nevertheless changes and modifications, which do not depart from the teachings herein, will be apparent to those of skill in the art. Such changes and modifications are deemed to fall within the purview of the invention as claimed.

REFERENCES

1. Jain, R. K., and L. T. Baxter. 1988. Mechanisms of heterogeneous distribution of monoclonal antibodies and other macromolecules in tumors: significance of elevated interstitial pressure. *Cancer Res* 48:7022-7032.
2. Tofts, P. S., and A. G. Kermode. 1991. Measurement of the blood-brain barrier permeability and leakage space using dynamic MR imaging. 1. Fundamental concepts. *Magn Reson Med* 17:357-367.
3. Tofts, P. S., and B. A. Berkowitz. 1994. Measurement of capillary permeability from the Gd enhancement curve: a comparison of bolus and constant infusion injection methods. *Magn Reson Imaging* 12:81-91.
4. Hassid, Y., E. Furman-Haran, R. Margalit, R. Eilar, and H. Degani. 2006. Noninvasive magnetic resonance imaging of transport and interstitial fluid pressure in ectopic human lung tumors. *Cancer Res* 66:4159-4166.
5. Au, J. L., S. H. Jang, J. Zheng, C. T. Chen, S. Song, L. Hu, and M. G. Wientjes. 2001. Determinants of drug delivery and transport to solid tumors. *J Control Release* 74:31-46.
6. Tannock, I. F., C. M. Lee, J. K. Tunggal, D. S. Cowan, and M. J. Egorin. 2002. Limited penetration of anticancer drugs through tumor tissue: a potential cause of resistance of solid tumors to chemotherapy. *Clin Cancer Res* 8:878-884.
7. Fukumura, D., and R. K. Jain. 2006. Tumor microenvironment abnormalities: Causes, consequences, and strategies to normalize. *J Cell Biochem.*
8. Desmouliere, A., C. Guyot, and G. Gabbiani. 2004. The stroma reaction myofibroblast: a key player in the control of tumor cell behavior. *Int J Dev Biol* 48:509-517.
9. Jain, R. K. 1987. Transport of molecules in the tumor interstitium: a review. *Cancer Res* 47:3039-3051.
10. Heldin, C. H., K. Rubin, K. Pietras, and A. Ostman. 2004. High interstitial fluid pressure—an obstacle in cancer therapy. *Nat Rev Cancer* 4:806-813.
11. Less, J. R, M. C. Posner, Y. Boucher, D. Borochovitz, N. Wolmark, and R. K. Jain. 1992. Interstitial hypertension in human breast and colorectal tumors. *Cancer Res* 52:6371-6374.
12. Nathanson, S. D., and L. Nelson. 1994. Interstitial fluid pressure in breast cancer, benign breast conditions, and breast parenchyma. *Ann Surg Oncol* 1:333-338.
13. Boucher, Y., J. M. Kirkwood, D. Opacic, M. Desantis, and R. K. Jain. 1991. Interstitial hypertension in superficial metastatic melanomas in humans. *Cancer Res* 51:6691-6694.
14. Curti, B. D., W. J. Urba, W. G. Alvord, J. E. Janik, J. W. Smith, 2nd, K. Madara, and D. L. Longo. 1993. Interstitial pressure of subcutaneous nodules in melanoma and lymphoma patients: changes during treatment. *Cancer Res* 53:2204-2207.
15. Gutmann, R., M. Leunig, J. Feyh, A. E. Goetz, K. Messmer, E. Kastenbauer, and R. K. Jain. 1992. Interstitial hypertension in head and neck tumors in patients: correlation with tumor size. *Cancer Res* 52:1993-1995.
16. Fyles, A., M. Milosevic, M. Pintilie, A. Syed, W. Levin, L. Manchul, and R. P. Hill. 2006. Long-term performance of interstitial fluid pressure and hypoxia as prognostic factors in cervix cancer. *Radiother Oncol* 80:132-137.
17. Milosevic, M., A. Fyles, D. Hedley, M. Pintilie, W. Levin, L. Manchul, and R Hill. 2001. Interstitial fluid pressure predicts survival in patients with cervix cancer independent of clinical prognostic factors and tumor oxygen measurements. *Cancer Res* 61:6400-6405.
18. Jirtle, R. L. 1981. Blood flow to lymphatic metastases in conscious rats. *Eur J Cancer* 17:53-60.
19. Horsman, M. R., K. L. Christensen, and J. Overgaard. 1992. Relationship between the hydralazine-induced changes in murine tumor blood supply and mouse blood pressure. *Int J Radiat Oncol Biol Phys* 22:455-458.
20. Stone, H. B., A. I. Minchinton, M. Lemmon, D. Menke, and J. M. Brown. 1992. Pharmacological modification of tumor blood flow: lack of correlation between alteration of mean arterial blood pressure and changes in tumor perfusion. *Int J Radiat Oncol Biol Phys* 22:79-86.
21. Quinn, P. K, M. C. Bibby, J. A. Cox, and S. M. Crawford. 1992. The influence of hydralazine on the vasculature, blood perfusion and chemosensitivity of MAC tumours. *Br J Cancer* 66:323-330.

22. Lee, C. G., M. Heijn, E. di Tomaso, G. Griffon-Etienne, M. Ancukiewicz, C. Koike, K. R. Park, N. Ferrara, R. K. Jain, H. D. Suit, and Y. Boucher. 2000. Anti-Vascular endothelial growth factor treatment augments tumor radiation response under normoxic or hypoxic conditions. *Cancer Res* 60:5565-5570.

23. Tong, R. T., Y. Boucher, S. V. Kozin, F. Winkler, D. J. Hicklin, and R. K Jain. 2004. Vascular normalization by vascular endothelial growth factor receptor 2 blockade induces a pressure gradient across the vasculature and improves drug penetration in tumors. *Cancer Res* 64:3731-3736.

24. Wildiers, H., G. Guetens, G. De Boeck, E. Verbeken, B. Landuyt, W. Landuyt, EA. de Bruijn, and A. T. van Oosterom. 2003. Effect of antivascular endothelial growth factor treatment on the intratumoral uptake of CPT-11. *Br J Cancer* 88:1979-1986.

25. Willett, C. G., Y. Boucher, E. di Tomaso, D. G. Duda, L. L. Munn, R. T. Tong, D. C. Chung, D. V. Sahani, S. P. Kalva, S. V. Kozin, M. Mino, K. S. Cohen, D. T. Scadden, A. C. Hartford, A. J. Fischman, J. W. Clark, D. P. Ryan, A. X. Zhu, L. S. Blaszkowsky, H. X. Chen, P. C. Sbellito, G. Y. Lauwers, and R. K. Jain. 2004. Direct evidence that the VEGF-specific antibody bevacizumab has antivascular effects in human rectal cancer. *Nat Med* 10: 145-147.

26. Eikenes, L., O. S. Bruland, C. Brekken, and L. Davies Cde. 2004. Collagenase increases the transcapillary pressure gradient and improves the uptake and distribution of monoclonal antibodies in human osteosarcoma xenografts. *Cancer Res* 64:4768-4773.

27. Fadnes, H. O., R. K. Reed, and K. Auldand. 1977. Interstitial fluid pressure in rats measured with a modified wick technique. *Microvasc Res* 14:27-36.

28. Jain, R. K. 2001. Delivery of molecular and cellular medicine to solid tumors. *Adv Drug Deltv Rev* 46:149-168.

29. Bhatnagar, A., R. Hustinx, and A Alavi. 2000. Nuclear imaging methods for non-invasive drug monitoring. *Adv Drug Deliv Rev* 41:41-54.

30. Matteucci, M. L., G. Anyarambhatla, G. Rosner, C. Azuma, P. E. Fisher, M. W. Dewhirst, D. Needham, and D. E. Thrall. 2000. Hyperthermia increases accumulation of technetium-99m-labeled liposomes in feline sarcomas. *Clin Cancer Res* 6:3748-3755.

31. Leander, P., S. Mansson, T. Ege, and J. Besjakov. 1996. CT and MR imaging of the liver using liver-specific contrast media A comparative study in a tumour model. *Acta Radiol* 37:242-249.

32. Suga, K., M. Mikawa, N. Ogasawara, H. Okazaki, and N. Matsunaga. 2001. Potential of Gd-DTPA-mannan liposome particles as a pulmonary perfusion MRI contrast agent: an initial animal study. *Invest Radiol* 36:136-145.

33. Dadiani, M., E. Furman-Haran, and H. Degani. 2006. The application of NMR in tumor angiogenesis research *Progress in NMR Spectroscopy* 49:27-44.

34. Padhani, A. R. 2002. Dynamic contrast-enhanced MRI in clinical oncology: current status and future directions. *J Magn Reson Imaging* 16:407-422.

35. Baxter, L. T., and R. K. Jain. 1989. Transport of fluid and macromolecules in tumors. I. Role of interstitial pressure and convection. *Microvasc Res* 37:77-104.

36. R ofitad, E. K., S. H. Tunheim, B. Mathiesen, B. A. Graff, E. F. Halsor, K. Nilsen, and K. Galappathi. 2002. Pulmonary and lymph node metastasis is associated with primary tumor interstitial fluid pressure in human melanoma xenografts. *Cancer Res* 62:661-664.

37. Boucher, Y., L. T. Baxter, and R. K. Jain. 1990. Interstitial pressure gradients in tissue-isolated and subcutaneous tumors: implications for therapy. *Cancer Res* 50:4478-4484.

38. Brekken, C., M. H. Hjelstuen, O. S. Bruland, and C. de Lange Davies. 2000. Hyaluronidase-induced periodic modulation of the interstitial fluid pressure increases selective antibody uptake in human osteosarcoma xenografts. *Anticancer Res* 20:3513-3519.

39. Netti, P. A., D. A. Berk, M. A. Swartz, A. J. Grodzinsky, and W. K. Jain. 2000. Role of extracellular matrix assembly in interstitial transport in solid tumors. *Cancer Res* 60:2497-2503.

40. Furman-Haran, E., D. Grobgeld, and H. Degani. 1997. Dynamic contrast-enhanced imaging and analysis at high spatial resolution of MCF7 human breast tumors. *J Magn Reson* 128:161-171.

41. Netti, P. A., L. T. Baxter, Y. Boucher, R. Skalak, and R. K. Jain. 1995. Time-dependent behavior of interstitial fluid pressure in solid tumors: implications for drug delivery. *Cancer Res* 55:5451-5458.

42. Netti, P. A., S. Roberge, Y. Boucher, L. T. Baxter, and R. K. Jain. 1996. Effect of transvascular fluid exchange on pressure-flow relationship in tumors: a proposed mechanism for tumor blood flow heterogeneity. *Microvasc Res* 52:27-46.

43. Baish, J. W., P. A. Netti, and R. K. Jain. 1997. Transmural coupling of fluid flow in microcirculatory network and interstitium in tumors. *Microvasc Res* 53:128-141.

44. Rosen, Y., G. Ramniceanu, R. Margalit, D. Grobgeld, R. Eilam, H. Degani, and E. Furman-Haran. 2006. Vascular perfusion of human lung cancer in a rat orthotopic model using dynamic contrastenhanced magnetic resonance imaging. *Int J Cancer* 119:365-372.

What is claimed is:

1. Apparatus for non-invasive mapping of actual interstitial fluid pressure in a mammal in space with time of a preselected location comprising: (a) an infuser for infusing a tracer/contrast-agent into a mammal that flows throughout the mammal, and, clears out from the mammal; (b) a monitor for monitoring a preselected location in a mammal for collecting data indicative of changes in tracer concentration with time and providing a first output; (c) a data processor including first circuitry responsive to the first output of the monitor for receiving and processing the collected data to obtain transfer constants and pressure gradients characteristic of a preselected location and providing a second output; (d) said data processor including a second circuitry for determining from the first and second outputs tracer concentration at steady state and differences in space of tracer concentration due to pressure gradients and providing a third output; (e) said second circuitry of said data processor being arranged and programmed with non-transitory instructions for determining concentration of contrast agent in a preselected volume on the basis of (i) if there are no pressure gradients in preselected volume, then determine concentration (C) varying with time (t) as $$C(t) = D_{inf} K_{in} \sum_{i=1}^{2} a_i \left( \frac{1 - e^{-\frac{K_{out}}{v_e}t}}{\frac{K_{out}}{v_e}} - \frac{1 - e^{-m_i t}}{m_i} \right) \Big/ \left( m_i - \frac{K_{out}}{v_e} \right) + v_p D_{inf} \sum_{i=1}^{2} a_i \left( \frac{1 - e^{-m_i t}}{m_i} \right)$$

where: $K_{in}$ and $K_{out}$ are transcapillary transfer constants into and out of tissue of the mammal and are equal to each other when only concentration gradients dictate transfer $K_{in} = K_{out} = K^{trans}$, $D_{inf}$ is total dose infused, $v_e$ is fraction of free volume in the tissue known as extracellular volume fraction, $v_p$ is an intravascular volume fraction and $a_i$, $m_i$ are amplitude and clearance time constant of the contrast agent in plasma of blood of the mammal;

(ii) if there are pressure gradients that enhance delivery to the preselected volume, determine concentration varying with time as $$C(t) = D_{inf}(K_{in} + K_{in}^p) \sum_{i=1}^{2} a_i \left( \frac{1 - e^{-\frac{K_{out}}{v_e}t}}{\frac{K_{out}}{v_e}} - \frac{1 - e^{-m_i t}}{m_i} \right) / \left( m_i - \frac{K_{out}}{v_e} \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{in}^p$ is a pressure transfer constant; and (iii) if there are pressure gradients that inhibit delivery to the preselected volume, determine concentration varying with time as $$C(t) = D_{inf} K_{in}$$

$$\sum_{i=1}^{2} a_i \left( \frac{1 - e^{-\left(\frac{K_{p_{out}} + K_{out}}{v_e}\right)t}}{\frac{K_{out}^p + K_{out}}{v_e}} - \frac{1 - e^{-m_i t}}{m_i} \right) / \left( m_i - \left(\frac{K_{out}^p + K_{out}}{v_e}\right) \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{out}^p$ is a convection term that washes the contrast agent outward away from the preselected volume;

(f) a mapper for receiving the second and third outputs and mapping pressure gradients in the preselected location for determining an efficacy of tracer delivery to a selected location and generating a fourth output; and memory for receiving and storing the fourth output.

2. Apparatus according to claim 1 wherein the monitor is an MRI system.

3. Apparatus according to claim 1 wherein one of a display and a printer is provided to receive the fourth output and visually display the fourth output as a map.

4. Apparatus according to claim 1 further including a means to control drug delivery responsive to the fourth output.

5. A computer readable medium encoded with non-transitory computer program instructions, the instructions program comprising monitoring a preselected location in a mammal for collecting data indicative of changes in tracer concentration with time and providing a first output; responsive to the first output for receiving collected data and processing to obtain transfer constants and pressure gradients characteristic of the preselected location and providing a second output; responsive to the first and second outputs for determining tracer concentration at steady state and differences in space of tracer concentration due to pressure gradients and providing a third output; for determining concentration of contrast agent in a preselected volume on basis of (i) if there are no pressure gradients in the preselected volume, then determining concentration (C) varying with time (t) as $$C(t) = D_{inf} K_{in} \sum_{i=1}^{2} a_i \left( \frac{1 - e^{-\frac{K_{out}}{v_e}t}}{\frac{K_{out}}{v_e}} - \frac{1 - e^{-m_i t}}{m_i} \right) / \left( m_i - \frac{K_{out}}{v_e} \right) + $$

$$v_p D_{inf} \sum_{i=1}^{2} a_i \left( \frac{1 - e^{-m_i t}}{m_i} \right)$$

where: $K_{in}$ and $K_{out}$ are transcapillary transfer constants into and out of tissue of the mammal and are equal to each other when only concentration gradients dictate a transfer $K_{in} = K_{out} = K^{trans}$, $D_{inf}$ is total dose infused, $v_e$ is a fraction of free volume in tissue as extracellular volume fraction, $v_p$ is an intravascular volume fraction and $a_i$, $m_i$ are amplitude and clearance time constant of the contrast agent in a plasma of a blood;

(ii) if there are pressure gradients that enhance delivery to the preselected volume, determining concentration varying with time as $$C(t) = D_{inf}(K_{in} + K_{in}^p) \sum_{i=1}^{2} a_i \left( \frac{1 - e^{-\frac{K_{out}}{v_e}t}}{\frac{K_{out}}{v_e}} - \frac{1 - e^{-m_i t}}{m_i} \right) / \left( m_i - \frac{K_{out}}{v_e} \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{in}^p$ is a pressure transfer constant; and (iii) if there are pressure gradients that inhibit delivery to the preselected volume, determining concentration varying with time as $$C(t) = D_{inf} K_{in}$$

$$\sum_{i=1}^{2} a_i \left( \frac{1 - e^{-\left(\frac{K_{p_{out}} + K_{out}}{v_e}\right)t}}{\frac{K_{out}^p + K_{out}}{v_e}} - \frac{1 - e^{-m_i t}}{m_i} \right) / \left( m_i - \left(\frac{K_{out}^p + K_{out}}{v_e}\right) \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{out}^p$ is a convection term that washes the contrast agent outward away from the preselected volume and responsive to the second and third outputs for deriving a fourth output indicative of pressure gradients in the preselected location that are indicative of drug delivery to a selected location.

6. A computer readable medium as in claim 5, wherein the computer readable medium encoded with further non-transitory computer program instructions executable responsive to the fourth output for mapping the fourth output, and providing a resultant map for display.

7. A computer readable medium as in claim 5, wherein the computer readable medium encoded with further non-transitory computer program instructions executable responsive to the fourth output for controlling drug delivery to the preselected location.

8. Method for monitoring non-invasively a human or animal actual interstitial fluid pressure in space with time comprising the steps of: (a) slowly infusing a contrast agent into a human or animal; (b) monitoring a preselected volume in the human or animal for collecting data indicative of interstitial fluid pressure that varies with time as a function of at least two variables related to contrast agent concentration and fluid pressure behavior; (c) processing collected data to determine actual interstitial fluid pressure throughout the preselected volume with time; and providing an output indicative of one of the determined actual interstitial fluid pressure and concentration of contrast agent; wherein the step of processing collected data to determine interstitial fluid pressure throughout the preselected volume with time includes determining pressure gradients; and including the further step of processing to determine concentration of contrast agent in the preselected volume on the basis of (i) if there are no pressure gradients in the preselected volume, then determine concentration varying with time as $$C(t) = D_{inf} K_{in} \sum_{i=1}^{2} a_i \left( \frac{1 - e^{-\frac{K_{out}}{v_e} t}}{\frac{K_{out}}{v_e}} - \frac{1 - e^{-m_i t}}{m_i} \right) \Big/ \left( m_i - \frac{K_{out}}{v_e} \right) +$$

$$v_p D_{inf} \sum_{i=1}^{2} a_i \left( \frac{1 - e^{-m_i t}}{m_i} \right)$$

where: $K_{in}$ and $K_{out}$ are transcapillary transfer constants into and out of tissue of the mammal and are equal to each other when only concentration gradients dictate a transfer $K_{in} = K_{out} = K^{trans}$, $D_{inf}$ is total dose infused, $v_e$ is a fraction of free volume in tissue as extracellular volume fraction, $v_p$ is an intravascular volume fraction and $a_i$, $m_i$ are amplitude and clearance time constant of the contrast agent in a plasma of a blood;
(ii) if there are pressure gradients that enhance delivery to the preselected volume, determining concentration varying with time as $$C(t) = D_{inf}(K_{in} + K_{in}^p) \sum_{i=1}^{2} a_i \left( \frac{1 - e^{-\frac{K_{out}}{v_e} t}}{\frac{K_{out}}{v_e}} - \frac{1 - e^{-m_i t}}{m_i} \right) \Big/ \left( m_i - \frac{K_{out}}{v_e} \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{in}^p$ is a pressure transfer constant; and
(iii) if there are pressure gradients that inhibit delivery to the preselected volume, determine concentration varying with time as $$C(t) = D_{inf} K_{in}$$

$$\sum_{i=1}^{2} a_i \left( \frac{1 - e^{-\left(\frac{K_{pout} + K_{out}}{v_e}\right) t}}{\frac{K_{out}^p + K_{out}}{v_e}} - \frac{1 - e^{-m_i t}}{m_i} \right) \Big/ \left( m_i - \left(\frac{K_{out}^p + K_{out}}{v_e}\right) \right) + +$$

$$v_p D_{inf} \sum_{i=1}^{2} a_i \left( \frac{1 - e^{-m_i t}}{m_i} \right)$$

wherein $K_{in} = K_{out} = K$ and $K_{out}^p$ is a convection term that washes the contrast agent outward away from the preselected volume.

9. The method according to claim 8 including the further step of graphically depicting the preselected volume in color to show one of interstitial fluid pressure and concentration of contrast agent.

10. The method according to claim 8 wherein the infusion of the contrast agent takes place slowly, at constant or varying rates.

11. The method of claim 8 including the further step of controlling delivery of a drug to the preselected volume responsive to the output of step (c).

12. The method of claim 11 including the further steps of detecting resistance to drug delivery and in response thereto administering to the human or animal a drug to lower the interstitial fluid pressure.

13. A computer system comprising a processor and a non-transitory computer readable storage medium storing readable instructions wherein execution of the instructions cause the processor to determine efficacy of a drug delivery to a preselected location in a human or animal by reflecting changes in actual interstitial fluid pressure in space with time after infusion of a tracer/contrast agent, and in response thereto to create at least one digitally encoded image on the computer readable medium based on a plurality of time intervals and being representative of, in two or three dimensions, one of interstitial fluid pressure and tracer/contrast agent concentration in a preselected location wherein discrete elements of the image have a color hue of one of a plurality of colors and a color intensity indicative of fluid pressure behavior, wherein a step of processing collected data to determine interstitial fluid pressure throughout a preselected volume with time includes determining pressure gradients; and including a further step of processing to determine concentration of contrast agent in the preselected volume on the basis of (i) if there are no pressure gradients in a preselected volume, then determine concentration varying with time as $$C(t) = D_{inf} K_{in} \sum_{i=1}^{2} a_i \left( \frac{1 - e^{-\frac{K_{out}}{v_e} t}}{\frac{K_{out}}{v_e}} - \frac{1 - e^{-m_i t}}{m_i} \right) \Big/ \left( m_i - \frac{K_{out}}{v_e} \right) +$$

$$v_p D_{inf} \sum_{i=1}^{2} a_i \left( \frac{1 - e^{-m_i t}}{m_i} \right)$$

where: $K_{in}$ and $K_{out}$ are transcapillary transfer constants into and out of tissue of the mammal and are equal to each other when only concentration gradients dictate a transfer $K_{in} = K_{out} = K^{trans}$, $D_{inf}$ is a total dose infused, $v_e$ is a fraction of free volume in tissue as extracellular volume fraction, $v_p$ is an intravascular volume fraction and $a_i$, $m_i$ are amplitude and clearance time constant of the contrast agent in a plasma of a blood;

(ii) if there are pressure gradients that enhance delivery to the preselected volume, determining concentration varying with time as $$C(t) = D_{inf}(K_{in} + K_{in}^P) \sum_{i=1}^{2} a_i \left( \frac{1 - e^{-\frac{K_{out}}{v_e}t}}{\frac{K_{out}}{v_e}} - \frac{1 - e^{-m_i t}}{m_i} \right) \bigg/ \left( m_i - \frac{K_{out}}{v_e} \right) ++$$

$$v_p D_{inf} \sum_{i=1}^{2} a_i \left( \frac{1 - e^{-m_i t}}{m_i} \right)$$

wherein $K_{in}=K_{out}=K$ and $K_{in}^P$ is a pressure transfer constant; and (iii) if there are pressure gradients that inhibit delivery to the preselected volume, determine concentration varying with time as $$C(t) = D_{inf} K_{in}$$

$$\sum_{i=1}^{2} a_i \left( \frac{1 - e^{-\left(\frac{K_{P_{out}}+K_{out}}{v_e}\right)t}}{\frac{K_{out}^P + K_{out}}{v_e}} - \frac{1 - e^{-m_i t}}{m_i} \right) \bigg/ \left( m_i - \left( \frac{K_{out}^P + K_{out}}{v_e} \right) \right) ++$$

$$v_p D_{inf} \sum_{i=1}^{2} a_i \left( \frac{1 - e^{-m_i t}}{m_i} \right)$$

wherein $K_{in}=K_{out}=K$ and $K_{out}^P$ is a convection term that washes the contrast agent outward away from the preselected volume.

14. The computer system of claim 13 wherein the readable instruction include instructions for displaying the at least one image on a display.

15. The computer system of claim 13 wherein the readable instruction include instructions for printing the at least one image on a printer.

* * * * *